US006566048B1

(12) United States Patent
Dixon et al.

(10) Patent No.: US 6,566,048 B1
(45) Date of Patent: May 20, 2003

(54) **ACETYL-COA-CARBOXYLASE FROM *CANDIDA ALBICANS***

(75) Inventors: Graham K Dixon, Macclesfield (GB); John L Thain, Macclesfield (GB); John P Vincent, Macclesfield (GB); Norbert F Schnell, Macclesfield (GB); Suberna J Chavda, Macclesfield (CA)

(73) Assignee: Syngenta Limited, London (GB)

( * ) Notice: Subject to any disclaimer, the term of this patent is extended or adjusted under 35 U.S.C. 154(b) by 0 days.

(21) Appl. No.: 09/581,909

(22) PCT Filed: Dec. 21, 1998

(86) PCT No.: PCT/GB98/03857

§ 371 (c)(1), (2), (4) Date: Jun. 19, 2000

(87) PCT Pub. No.: WO99/32635

PCT Pub. Date: Jul. 1, 1999

(30) Foreign Application Priority Data

Dec. 20, 1997 (GB) .......................................... 9726897

(51) Int. Cl.[7] ........................... C12Q 1/00; C12N 9/00; C12N 1/20; C12N 15/00; C07K 7/00

(52) U.S. Cl. ....................... 435/4; 435/183; 435/252.3; 435/320.1; 435/325; 536/23.2; 530/350

(58) Field of Search ............................ 435/183, 320.1, 435/252.3, 4; 536/232

(56) References Cited

FOREIGN PATENT DOCUMENTS

| | | |
|---|---|---|
| FR | 2 727 129 | 5/1996 |
| GB | 2 137 208 | 10/1984 |

OTHER PUBLICATIONS

Al–Feel W Et Al: "Cloning of the yeast FAS3 gene and primary structure of yeast acetyl–CoA carboxylase" Proceedings of the National Academy of Sciences of USA, vol. 89, May 1992, pp. 4534–4538, XP002097900 Washington US see the whole document.

Horikawa S Et Al: "Cell–Free Translation and Regulation of Candida–Lipolytica Acetyl Coenzyme a Carboxylase ES–6. 4:1.2 Messenger RNA." Eur. J Biochem, (1980) 104 (1) 191–198. CODEN: EJBCAI. ISSN: 0014–2956., XP002097901.

See the attached commercial database search results.*

Geneseg Database, Accession No. AAQ93232, Feb. 1996.*

* cited by examiner

*Primary Examiner*—M. Monshipouri
(74) *Attorney, Agent, or Firm*—Ropes & Gray

(57) ABSTRACT

The Acetyl-COA-carboxylase (ACCase) gene from *Candida albicans.*

19 Claims, 6 Drawing Sheets

GCACGCTTGACGGTTTTCACCAAATGCGAAAATATGACCAAATTGAGAATCCGAAAATGA
ATGGATAGAAGATTGGTTACCAACTGAGAAATAACCCCACACATTAGAAGAAGAACGGAA
ATTCAATTCATGTAAAGAACCACCACTTGGTTTAAAACCTTCACCAGGATCTTCAGAAGT
AATACGACAAGCAGTACAATGTCCCTTTGGTGTTGGTCTTCTTTGACTAACCAATGAAGT
TTCTGACTTGAATTCAAAATCAATATCAGTAGTGGTATGAGGATCGGCACCGCACAAAGT
TCTGATATCTCTGATTCTATGCATTGGTATACCCATAGCAATTTGTAATTGAGCAGCTGG
TAAATTAACACCTGTCACCATTTCAGTGGTTGGATGTTCAACTTGCAATCTTGGGTTCAA
TTCCAAAAAGTAGAATTTATCTTCAGCGTGGGGAGTAAAGGTACTCAACAGTACCAGGGG
GTTACATAACCAACTTATTTTACCCAATCTGACTGGTGGATTT

Fig. 1

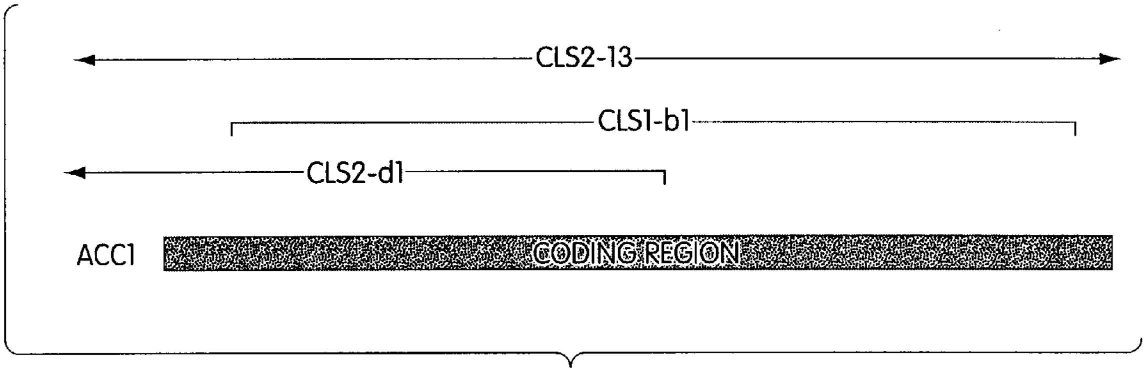

Fig. 2

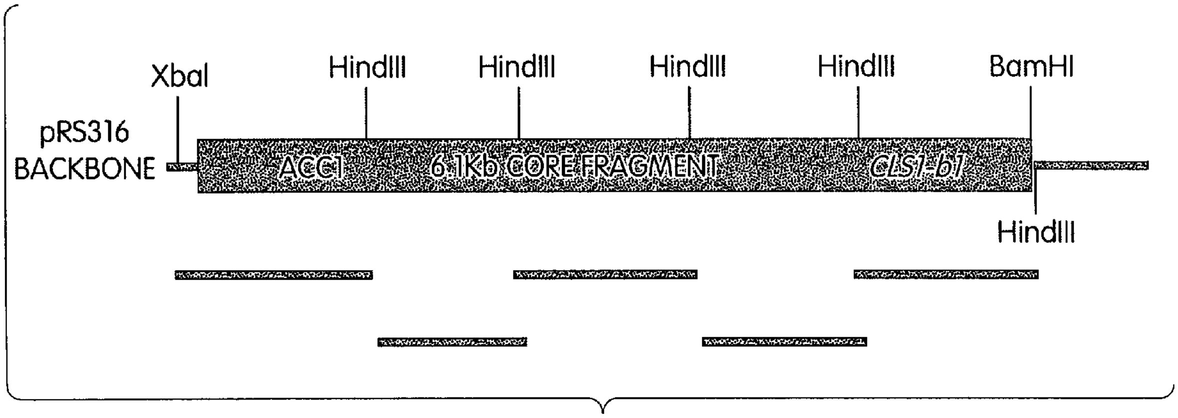

Fig. 3

AATATATTGCTTCCTTTTGATAGGAAGTAACTCCGAGTGTTTGAATTTGATATATGTTATTCATATACGTTCAATGGCTC
TCTTCTATGCTTTGTATATACTTTCTTTTGAATAGATACTCATGTAAAGAGATTTGAAACCATATTCTAACCAACAAAAA
TATTGTACGGTATAGGTTAGAAAAAAAACTCCGTAAGGTCCGCTTACACGGTTAAATTGAAAACACGTTAAAAATATATT
TGGGTAATGGACTAAGCTATATACAGTACTCAACAAAAATGAAATCAAACACAATGTTCTTTGGGAAATTCATTTCATGC
AACTAGGGTGATTCTCTTTCTACTATCCAACAACGATAACCCTGCTTTTGAAAAATCTTTTCTAAATTCAAATTGATATA
ATTCTTATTTATATATTACTTTCTTTTTCCCATATAACCCCATTTTTTTTTTGGAATCATATTTGTTTTTGATTTTTGCT
TTCCCTTTCAGTCTGAGGAACATACTAATTACGAACAACAATTATACATCCAATCTTCATCTAACGAATTGATTATTTAC
ATTTATTAAACCCTTGGATACAAACTGATTACACTTTTTAGTTAGTTTGTTCAATTATAAGGGTATTATACAACAAAGAT
ATCATTTAAAGTTAAATCTCAATCTGGAATAATAAAAGTATTCAACACTTTTGCTTACAATAGGTATGTTCAAAATCAAT
TGAAGCCATCGAGATAAGAAATTAAGCAAAAACGTTTACAATTGTTGTGTGTGTGTTGCAGTGTTTGAAGAAGCTCGAGT
GATTGCTTTTCTTCGGCATCAGCTGTGTTGGGAACATCTTGTCGTTAAAGTTTCGGAGTAATATTAGAGTAATGGAACGA
AAAAAACAAAATAAAGTTCTGGAACCACAAAGATTTGAAAAATTGGGTAGAAACAAAAAAAAGACAAAGCAGGAACCCAA
CAATAAATGAATAAACACTCAAAAACTACTCACAACAACAACACTTATTTTCACTTGCTTTATTTCTTCGATTTTTTatg
AGATGCAAATTATCTCTAATAAAGAATACTAACTCACTTGTACATAGATCGCGTTTCCTAATTACAAAACCACAACTATA
TATACCTCATCGTCATTATATCCCATTCAAGAACATATTCAAGTCATTGTTAatgTCAGATCAATCTCCATCTCCTAGTC
CTAGCGATTCCCTTAGCTACACTACATTACATGAAAATTTGCCATCTCATTTCTTGGGTGGAAATTCAGTTTTGAATGCT
GAACCTTCTAAAGTCAGAGACTTTGTCAGAGCTCATCAAGGTCATACAGTTATTTCGAAAATTTTAATTGCCAACAATGG
TATAGCTGCAGTTAAAGAAATCAGATCAGTTAGAAAATGGGCTTATGAAACATTTGGTGACGAAAAAGCCATACAGTTTA
CCGTTATGGCCACTCCAGAAGATTTGGAAGCTAATGCCGAATATATTAGAATGGCCGACCAATTCATTGAAGTCCCTGGT
GGCACCAATAACAATAACTATGCTAATGTTGATCTCATTGTAGAGATAGCAGAAAGTACAAATGCTCATGCCGTTTGGGC
TGGGTGGGGGCATGCTTCAGAGAATCCTTTGTTACCAGAAAAATTAGCTGCATCTCCCAAAAAAATTATTTTTATTGGTC
CTCCTGGTTCAGCTATGAGATCTTTAGGTGACAAGATTTCATCTACTATAGTTGCTCAACATGCTCAAGTACCATGTATT
CCATGGTCCGGTACTGGTGTTGATGAAGTGAAAATAGACCCACAAACTAATTTGGTTTCTGTTGCTGATGATATTTATGC
CAAAGGGTGCTGTACTAGTCCAGAAGATGGTTTAGAAAAAGCCAAAAAAATTGGGTTCCCAGTTATGATTAAAGCCTCTG
AAGGTGGTGGTGGTAAAGGTATTAGAAAAGTTGATGATGAGAAAAACTTCATTACCTTATACAACCAAGCAGCTAATGAA
ATACCAGGTTCTCCTATCTTTATTATGAAGTTAGCAGGTGATGCCAGACATTTAGAAGTTCAATTACTAGCAGATCAATA
CGGTACTAACATTTCCCTTTTTGGAAGAGATTGTTCCGTACAAAGAAGACACCAAAAGATTATTGAAGAAGCACCAGTCA
CCATTGCCAGAAAGGAAACTTTCCACGAAATGGAAAATGCAGCAGTCAGATTGGGTAAATTAGTTGGTTATGTATCCGCT
GGTACTGTTGAGTATCTTTACTCCCACGCTGAAGATAAATTCTACTTTTTGGAATTGAACCCAAGATTGCAAGTTGAACA
TCCAACCACTGAAATGGTGACAGGTGTTAATTTACCAGCTGCTCAATTACAAATTGCTATGGGTATACCAATGCATAGAA
TCAGAGATATCAGAACTTTGTACGGTGCCGATCCTCATACCACTACTGATATTGATTTTGAATTCAAGTCAGAAACTTCA
TTGGTTAGTCAAAGAAGACCAACACCAAAGGGACATTGTACTGCTTGTCGTATTACTTCTGAAGATCCTGGTGAAGGTTT
TAAACCAAGTGGTGGTTCTTTACATGAATTGAATTTCCGTTCTTCTTCTAATGTGTGGGGTTATTTCTCAGTTGGTAACC
AATCTTCTATCCATTCATTTTCGGATTCTCAATTTGGTCATATTTTCGCATTTGGTGAAAACCGTCAAGCTTCAAGAAAA
CATATGGTTGTTGCCTTGAAAGAATTGAGTATTAGAGGTGATTTTAGAACTACTGTTGAGTATTTAATCAAATTGTTAGA
AACTCCAGATTTCGAGGATAATACCATTACAACTGGTTGGTTGGATGAATTAATCACCAAAAAGTTGACTGCTGAAAGAC
CAGATCCAATAGTTGCTGTTGTTTGTGGAGCTGTAACCAAAGCACACATCCAGGCTGAGGAAGAGAAAAAGGAATACATC
CAATCTTTGGAAAAAGGTCAAGTTCCTCACAGAAACTTATTGAAAACTATTTTCCCAGTTGAGTTTATTTATGAAGGTGA
AAGATACAAGTTCACTGCTACTAAATCTTCAGAAGATAAATATACTTTGTTCCTTAATGGTTCTCGTTGTGTTGTTGGTG
CACGTTCATTGTCCGATGGTGGTTTATTGTGTGCATTAGATGGGAAATCACATTCTGTCTATTGGAAGGAAGAGGCATCT
GCCACTAGATTATCAGTTGATGGCAAAACTTGTTTATTAGAAGTTGAAAATGATCCAACACAATTAAGAACTCCATCTCC
AGGTAAATTGGTCAAGTATTTGGTTGACAGTGGTGAACATGTTGATGCTGGTCAACCATACGCTGAAGTCGAAGTTATGA
AAATGTGTATGCCTTTGATTGCTCAAGAAAATGGGGTAGTGCAGTTGATTAAACAACCGGGTTCCACAGTTAATGCTGGT
GATATCTTGGCCATTTTGGCATTGGACGATCCATCTAAGGTCAAACATGCTAAACCATTTGAAGGTACTTTACCATCTAT
GGGTGAGCCAAATGTTACAGGTACTAAACCAGCACATAAATTCAATCATTGTGCTGGTATTTTGAAAAACATTTTGGCTG
GTTATGATAATCAAGTGATTTTGAATTCTACTTTAAAGAGTCTTGGTGAAGTTTTGAAAGACAATGAATTGCCATACTCT
GAATGGCAACAACAAATTTCAGCTTTACACTCCAGATTGCCACCTAAATTGGATGACGGATTGACTGCATTGGTTGAAAG
AACTCAAAGTAGAGGTGCTGAATTCCCTGCTCGTCAAATTTTAAAACTCATCACCAAATCAATTGCTGAAAATGGTAATG
ATATGTTAGAAGATGTTGTTGCACCATTGGTTTCTATTGCCACAAGTTACCAGAATGGTTTGGTTGAACACGAATACGAT
TACTTTGCATCTTTGATTAACGAATATTATGACGTTGAAAGTTTGTTTTCAGGTGAAAATGTTAGAGAAGATAATGTTAT
CTTGAAATTAAGAGATGAAAACAAATCTGATTTGAAAAAAGTTATTGGTATTGGTTTGTCTCATTCACGTGTTAGTGCCA
AGAACAATTTGATTTTAGCTATTTTGGACATTTATGAACCATTGTTGCAATCCAACTCGTCAGTTGCTGCCTCTATCAGA
GAAGCTTTAAAGAACTTGTTCATTAGACCTCGTGCTTGTGCCAAAGTTGCATTAAAGGCAAGAGAAATTTTAATTCAATG

Fig. 4A

TTCTTTACCTTCCATCAAGGAAAGATCCGATCAATTGGAACATATTTTGAGGTCATCTGTTGTTCAAACCTCTTATGGTG
AAATTTTTGCTAAACATAGAGAACCAAATTTGGAAATTATTCGTGAGGTTGTTGATTCCAAACATATTGTTTTTGATGTG
TTGGCACAATTCTTAATCAATCCAGACCCATGGGTTGCCATTGCTGCCGCTGAAGTTTATGTCAGACGTTCATACCGTGC
TTATGATTTGGGTAAAATTGAATATCATGTTAATGACAGACTTCCTATTGTTGAATGGAAATTCAAGTTGGCTAATATGG
GAGCCGCTGGTGTAAACGATGCTCAACAGGCTGCTGCTGCCGGTGGCGATGATTCGACATCTATGAAACATGCAGCTTCT
GTGTCTGATTTGACCTTTGTTGTTGATTCTAAAACCGAGCATTCCACAAGAACTGGTGTTTTAGCTCCAGCAAGACACTT
GGATGATGTTGATGAAACTCTTACAGCTGCATTGGAACAATTCCAACCAGCCGATGCTATTTCATTTAAAGCAAAGGGTG
AAACTCCAGAGTTATTAAATGTTTTGAATATTGTCATTACCAGTATTGATGGTTACTCCGATGAAAATGAATACTTGAGC
AGAATTAATGAAATCTTGTGCGAATACAAAGAAGAGTTGATTTCTGCTGGTGTTCGTCGTGTTACATTTGTTTTTGCTCA
TCAAATTGGTCAATATCCTAAATATTATACTTTTACTGGTCCTGACTATGAAGAAAACAAGGTTATTAGACACATTGAAC
CAGCTTTGGCTTTCCAATTGGAATTGGGAAGATTAGCCAATTTCGATATCAAACCAATTTTCACTAACAACAGAAACATC
CATGTATATGATGCAATTGGGAAGAATGCTCCTTCTGATAAAAGATTTTTCACCAGAGGGATTATTAGAACCGGTGTTCT
TAAAGAAGACATTAGCATTAGTGAATATTTGATTGCTGAATCCAACAGATTAATGAATGATATTTTGGATACTTTAGAAG
TTATTGACACTTCTAATTCTGATTTAAACCATATTTTCATTAACTTTTCCAATGCTTTCAATGTTCAAGCTTCAGATGTT
GAGGCTGCCTTTGGATCATTCTTAGAAAGATTTGGTAGAAGATTATGGAGATTAAGAGTTACTGGTGCTGAAATTAGAAT
TGTCTGTACTGATCCTCAAGGTACTTCGTTCCCATTGCGTGCTATCATTAATAATGTTTCTGGTTATGTTGTCAAATCAG
AATTGTATTTGGAAGTGAAAAATCCTAAAGGTGAATGGGTTTTCAAATCCATTGGTCATCCTGGTTCCATGCATTTGAGA
CCTATCTCAACTCCATATCCAGTTAAAGAATCTTTACAACCAAAACGTTACAAGGCTCACAATATGGGTACCACTTATGT
GTATGACTTCCCAGAATTGTTTCGTCAAGCAACAATTTCACAATGGAAAAAATATGGCAAAAAAGTACCAAAAGATGTTT
TCGTGTCTTTAGAATTGATCACTGATGAAACTGATTCCTTAATAGCTGTTGAAAGAGATCCGGGTGCTAACAAAATTGGA
ATGGTTGGATTCAAAGTCACTGCTAAAACTCCTGAATACCCTCATGGTCGTCAATTAATTATTGTTGCCAATGATATCAC
CCACAAGATTGGTTCTTTTGGTCCAGAAGAAGATAATTATTTCAACAAGTGTACTGAATTGGCCAGAAAATTAGGTATTC
CAAGAATTTACCTTTCTGCAAATTCAGGTGCTAGAATTGGTGTTGCTGAGGAATTGATTCCATTATACCAAGTTGCCTGG
AATGAAGAAGGGTCTCCTGACAAAGGATTCAGATACTTGTACTTGAGTACTGCTGCTAAAGAGTCTTTAGAAAAAGATGG
TAAAAGTGACAGTGTTGTTACTGAACGTATTGTTGAAAAAGGTGAAGAGCGTCATGTCATTAAAGCTATTATTGGTGCCG
AAGATGGCTTAGGGGTTGAATGTCTTAAAGGATCAGGTTTAATTGCTGGTGCCACATCAAGAGCTTACAAGGATATATTT
ACCATCACTTTGGTAACTTGTAGATCTGTTGGTATTGGTGCTTATTTGGTTAGATTGGGTCAAAGAGCCATTCAAATCGA
TGGTCAACCTATTATTTTAACTGGTGCTCCTGCTATCAATAAATTGTTGGGTAGAGAAGTGTATTCTTCCAATCTTCAAT
TGGGTGGTACTCAAATCATGTACAATAATGGTGTTTCTCATTTGACAGCTAATGATGATTTGGCTGGGGTTGAAAAAATT
ATGGAATGGTTATCATATGTTCCAGCTAAACGTGGTTTACCAGTGCCAATTTTGGAATCAGAAGATTCTTGGGACAGAGA
TGTTGATTACTACCCACCAAAACAAGAAGCTTTTGATGTTAGATGGATGATCCAAGGTAGAGAAGTTGATGGTGAATATG
AATCTGGGTTATTTGATAAAGATTCATTCCAAGAAACATTATCTGGTTGGGCTAAAGGTGTTGTTGTTGGTAGAGCACGT
TTGGGTGGTATTCCAATTGGTGTTATTGGTGTCGAAACCAGAACAGTGGAAAACTTGATTCCTGCTGATCCAGCAAATCC
AGACTCTACAGAAAGTTTGATTCAAGAAGCAGGTCAAGTGTGGTATCCTAACTCTGCTTTTAAGACAGCACAAGCTATAA
ATGATTTCAACAATGGTGAACAATTGCCATTAATGATTTTAGCAAATTGGAGAGGTTTCTCTGGTGGTCAAAGAGATATG
TACAATGAAGTCTTGAAATATGGTTCATTTATTGTTGATGCTTTAGTTGACTTCAAGCAACCTATCTTCACTTACATTCC
ACCAAATGGAGAATTGAGAGGTGGCTCTTGGGTTGTTGTTGATCCAACCATCAACTCAGATATGATGGAAATGTATGCCG
ATGTCGATTCGAGAGCTGGTGTTTTGGAACCAGAAGGTATGGTTGGTATCAAATACAGACGTGATAAATTATTAGCAACT
ATGGAAAGATTAGATCCAACTTATGGTGAAATGAAAGCTAAGTTAAATGACTCGTCATTATCTCCAGAAGAACACTCGAA
AATAAGCGCCAAATTGTTTGCACGTGAAAAGGCTTTATTACCAATTTATGCTCAAATTTCCGTTCAATTTGCTGACTTGC
ACGATAGATCAGGTCGTATGTTGGCCAAGGGAGTTATTAGAAAGGAAATCAAATGGACTGATGCTAGACGTTTCTTCTTC
TGGAGATTGAGAAGAAGATTGAACGAGGAATATGTTTTGAGATTGATTAGTGAACAAATTAAAGATTCTAGCAAATTGGA
AAGAGTTGCCAGATTGAAGAGTTGGATGCCAACTGTTGAATACGATGATGACCAAGCTGTCAGTAACTGGATTGAAGAGA
ACCATGCCAAATTGCAAAAGAGAGTTAATGAATTGAAACAAGAAGTTTCAAGAACCAAGATTATGAGATTATTAAAAGAG
GATCCAAATAGTGCAATTTCTGCAATGAAAGACTATGTTGAAAGATTGTCAAAAGAAGATAAAGAGAAATTCCTCAAGGC
ATTGAAG<u>tag</u>AAGTGGTTTCCATTAATTCAACTTTTAATGACATTGAAAGTAGTAGTAGTTGTTGTTTTTTAGATTTAA
GTATATTATATTATGTAATAAATTATAGAAAGTAATTATAGTTTTGACGGTTAATTGACGAGAGTGGAAATTGGCTTTT
TTGTTGCTCGTGTGATGAAACAGTGATTGACACAAAAAAATAGACAATGAAAAC

Fig. 4B

MRCKLSLIKNTNSLVHRSRFLITKPQLYIPHRHYIPFKNIFKSLLMSDQSPSPSPSDSLSYTTLHENLPSHFLGGNSVLN
AEPSKVRDFVRAHQGHTVISKILIANNGIAAVKEIRSVRKWAYETFGDEKAIQFTVMATPEDLEANAEYIRMADQFIEVP
GGTNNNNYANVDLIVEIAESTNAHAVWAGWGHASENPLLPEKLAASPKKIIFIGPPGSAMRSLGDKISSTIVAQHAQVPC
IPWSGTGVDEVKIDPQTNLVSVADDIYAKGCCTSPEDGLEKAKKIGFPVMIKASEGGGGKGIRKVDDEKNFITLYNQAAN
EIPGSPIFIMKLAGDARHLEVQLLADQYGTNISLFGRDCSVQRRHQKIIEEAPVTIARKETFHEMENAAVRLGKLVGYVS
AGTVEYLYSHAEDKFYFLELNPRLQVEHPTTEMVTGVNLPAAQLQIAMGIPMHRIRDIRTLYGADPHTTTDIDFEFKSET
SLVSQRRPTPKGHCTACRITSEDPGEGFKPSGGSLHELNFRSSSNVWGYFSVGNQSSIHSFSDSQFGHIFAFGENRQASR
KHMVVALKELSIRGDFRTTVEYLIKLLETPDFEDNTITTGWLDELITKKLTAERPDPIVAVVCGAVTKAHIQAEEEKKEY
IQSLEKGQVPHRNLLKTIFPVEFIYEGERYKFTATKSSEDKYTLFLNGSECVVGARSLSDGGLLCALDGKSHSVYWKEEA
SATRLSVDGKTCLLEVENDPTQLRTPSPGKLVKYLVDSGEHVDAGQPYAEVEVMKMCMPLIAQENGVVQLIKQPGSTVNA
GDILAILALDDPSKVKHAKPFEGTLPSMGEPNVTGTKPAHKFNHCAGILKNILAGYDNQVILNSTLKSLGEVLKDNELPY
SEWQQQISALHSRLPPKLDDGLTALVERTQSRGAEFPARQILKLITKSIAENGNDMLEDVVAPLVSIATSYQNGLVEHEY
DYFASLINEYYDVESLFSGENVREDNVILKLRDENKSDLKKVIGIGLSHSRVSAKNNLILAILDIYEPLLQSNSSVAASI
REALKNLFIRPRACAKVALKAREILIQCSLPSIKERSDQLEHILRSSVVQTSYGEIFAKHREPNLEIIREVVDSKHIVFD
VLAQFLINPDPWVAIAAAEVYVRRSYRAYDLGKIEYHVNDRLPIVEWKFKLANMGAAGVNDAQQAAAAGGDDSTSMKHAA
SVSDLTFVVDSKTEHSTRTGVLAPARHLDDVDETLTAALEQFQPADAISFKAKGETPELLNVLNIVITSIDGYSDENEYL
SRINEILCEYKEELISAGVRRVTFVFAHQIGQYPKYYTFTGPDYEENKVIRHIEPALAFQLELGRLANFDIKPIFTNNRN
IHVYDAIGKNAPSDKRFFTRGIIRTGVLKEDISISEYLIAESNRLMNDILDTLEVIDTSNSDLNHIFINFSNAFNVQASD
VEAAFGSFLERFGRRLWRLRVTGAEIRIVCTDPQGTSFPLRAIINNVSGYVVKSELYLEVKNPKGEWVFKSIGHPGSMHL
RPISTPYPVKESLQPKRYKAHNMGTTYVYDFPELFRQATISQWKKYGKKVPKDVFVSLELITDETDSLIAVERDPGANKI
GMVGFKVTAKTPEYPHGRQLIIVANDITHKIGSFGPEEDNYFNKCTELARKLGIPRIYLSANSGARIGVAEELIPLYQVA
WNEEGSPDKGFRYLYLSTAAKESLEKDGKSDSVVTERIVEKGEERHVIKAIIGAEDGLGVECLKGSGLIAGATSRAYKDI
FTITLVTCRSVGIGAYLVRLGQRAIQIDGQPIILTGAPAINKLLGREVYSSNLQLGGTQIMYNNGVSHLTANDDLAGVEK
IMEWLSYVPAKRGLPVPILESEDSWDRDVDYYPPKQEAFDVRWMIQGREVDGEYESGLFDKDSFQETLSGWAKGVVVGRA
RLGGIPIGVIGVETRTVENLIPADPANPDSTESLIQEAGQVWYPNSAFKTAQAINDFNNGEQLPLMILANWRGFSGGQRD
MYNEVLKYGSFIVDALVDFKQPIFTYIPPNGELRGGSWVVVDPTINSDMMEMYADVDSRAGVLEPEGMVGIKYRRDKLLA
TMERLDPTYGEMKAKLNDSSLSPEEHSKISAKLFAREKALLPIYAQISVQFADLHDRSGRMLAKGVIRKEIKWTDARRFF
FWRLRRRLNEEYVLRLISEQIKDSSKLERVARLKSWMPTVEYDDDQAVSNWIEENHAKLQKRVNELKQEVSRTKIMRLLK
EDPNSAISAMKDYVERLSKEDKEKFLKALK

Fig. 5

ACETYL-COA-CARBOXYLASE FROM *CANDIDA ALBICANS*

This application is the national phase of international application PCT/GB98/03857 filed Dec. 21, 1998 which designated the U.S.

The present invention relates to Acetyl-COA-carboxylase (ACCase) genes from *Candida Albicans* (*C. albicans*) and methods for its expression. The invention also relates to novel hybrid organisms for use in such expression methods.

*C. albicans* is an important fungal pathogen and the most prominent target organism for antifungal research. ACCase is an enzyme of fatty acid biosynthesis and essential for fungal growth and viability. Inhibitors of the ACCase enzyme should therefore be potent antifungals. The ACCase proteins in all organisms are homologous to each other but they also differ significantly in the amino acid sequence. Because selectivity problems (for example fungal versus human) it is extremely important to optimise potential inhibitor leads directly against the target enzyme (*C. albicans*) and not against a homologous but non-identical model protein, for example from *Saccharomyces cerevisiae* (*S. Cerevisiae*).

We have now successfully cloned the ACCase gene from *C. albicans* (hereinafter referred to as the *C. Albicans* ACC1 gene) and elucidated its full length DNA sequence and corresponding polypeptide sequence, as set out in FIGS. 4 and 5 of this application respectively. The coding DNA sequence of the *C. Albicans* ACC1 gene is 6810 nucleotides in length and the corresponding protein sequence is 2270 amino acids in length. As will be explained below there are two forms of the *C. Albicans* ACC1 gene, the above numbers relate to the longer version, Met1.

Therefore in a first aspect of the present invention we provide a polynucleotide encoding a *C.albicans* ACCase gene, in particular the (purified) *C. albicans* ACC1 gene as set out in FIG. 5 hereinafter. It will be appreciated that the polynucleotide may comprise any of the degenerate codes for a particular amino acid including the use of rare codons. The polynucleotide is conveniently as set out in FIG. 4. It will be apparent from FIG. 4 that the gene is characterised by the start codons Met1 and Met2 (as indicated by the first and second underlined at codons, hereinafter referred to as atg1 and atg2 respectively). Both forms of the gene starting from Met1 and Met2 respectively are comprised in the present invention. The invention further comprises convenient fragments of any one of the above sequences. Convenient fragments may be defined by restriction endonuclease digests of sequence, suitable fragments include a full length *C. Albicans* ACC1 gene (starting with Met1 or Met2) flanked by unique Stul (5'-end)-NotI (3'-end) restriction sites as detailed in FIG. 6.

We also provide a polynucleotide probe comprising any one of the above sequences or fragments together with a convenient label or marker, preferably a non-radioactive label or marker. Following procedures well known in the art, the probe may be used to identify corresponding nucleic acid sequences. Such sequences may be comprised in libraries, such as cDNA libraries. We also provide RNA transcripts corresponding to any of the above *C. Albicans* ACC1 sequences or fragments.

In a further aspect of the invention we provide a *C. albicans* ACC1 enzyme, especially the ACC1 enzyme having the polypeptide sequence set out in FIG. 5, in isolated and purified form. This is conveniently achieved by expression of the coding DNA sequence of the *C. Albicans* ACC1 gene set out in FIG. 4, using methods well known in the art (for example as described in the Maniatis cloning manual—Molecular Cloning: A Laboratory Manual, $2^{nd}$ Edition 1989, J. Sambrook, E. F. Fritsch & Maniatis). As indicated for FIG. 4 above, the enzyme is characterised by two forms Met1 and Met2. Both form of the enzyme are comprised in the present invention.

The *C. Albicans* ACC1 enzyme of the present invention is useful as a target in biochemical assays. However, to provide sufficient enzyme for a biochemical assay for *C. Albicans* ACC1 (for example, for a high throughput screen for enzyme inhibitors) this has to be purified. Two major constraints impair this purification.

1) any new organism will necessitate deviation from published procedures because it will differ in its lysis and protease activity. *C. albicans* is known to express and secrete many aspartyl proteases.
2) The expression of *C. Albicans* ACC1 is very low and satisfying purification results can only be achieved if the enzyme is overexpressed.

We have now been able to overcome these problems by controlled overexpression of the *C. albicans* ACC1 in a Saccharomyces strain. This means that subsequent purification of the enzyme may then for example follow published procedures.

Therefore in a further aspect of the present invention we provide a novel expression system for expression of a *C. albicans* ACC1 gene which system comprises an *S. cerevisiae* host strain having a *C. albicans* ACC1 gene inserted in place of the native ACC1 gene from *S. Cerevisiae*, whereby the *C. albicans* ACC1 gene is expressed. Preferred *S. cerevisiae* strains include JK9-3Daα and its haploid segregants.

The *C. albicans* ACC1 gene is preferably over-expressed relative to that as may be achieved by a *C. albicans* wild type strain, ie under the control of its own ACC1 promoter. Whilst we do not wish to be bound by theoretical considerations, we have achieved approximately 14 fold over-expression relative to the wild-type host *S. cervisiae* strain JK9-3D. This may be achieved by replacing the *C. albicans* promoter in the expression construct by a stronger and preferably inducible promoter such as the *S. cerevisiae* GAL1 promoter.

Controlled overexpression is used to improve expression of a *C. albicans* polypeptide relative to expression under the control of a *C. albicans* promoter. In addition using procedures outlined in the accompanying examples we have been able to isolate a fully functional *C. albicans* ACC1 gene as determined by 100% inhibition by SoraphenA.

The novel expression system is conveniently prepared by transformation of a heterozygous ACC1 deletion strain of a convenient *S. cerevisiae* host by a convenient plasmid comprising the *C. albicans* ACC1 gene. Transformation is conveniently effected using methods well known in the art of molecular biology (Ito et al. 1983).

The plasmid comprising the *C. albicans* ACC1 gene and used to transform a convenient *S. cerevisiae* host represents a further aspect of the invention. Preferred plasmids for insertion of the *C. Albicans* ACC1 gene include YEp24, pRS316 and pYES2(Invitrogen).

The heterozygous ACC1 deletion strain of a convenient (diploid) *S. cerevisiae* host is conveniently achieved by disruption preferably using an antibiotic resistance cassette such as the kanamycin resistance cassette described by Wach et al (Yeast, 1994, 10, 1793–1808).

The expression systems of the invention may be used together with, for example cell growth and enzyme isolation procedures identical to or analogous to those described herein, to provide an acetyl-COA-carboxylase (ACCase) gene from *C. albicans* in sufficient quantity and with sufficient activity for compound screening purposes.

In a further aspect of the invention we provide the use of an acetyl-COA-carboxylase (ACCase) gene from *C. albicans* in assays to identify inhibitors of the polypeptide. In particular we provide the their use in pharmaceutical or agrochemical research.

As presented above the *C. albicans* ACC1 enzyme may be used in biochemical assays to identify agents which modulate the activity of the enzyme. The design and implementation of such assays will be evident to the biochemist of ordinary skill. The enzyme may be used to turn over a convenient substrate whilst incorporating/losing a labelled component to define a test system. Test compounds are then introduced into the test system and measurements made to determine their effect on enzyme activity. Particular assays are those used to identify inhibitors of the enzyme useful as antifungal agents. By way of non-limiting example, the activity of the ACC1 enzyme may be determined by (i) following the incorporation ($HCO_3$, Acetyl-CoA) or loss (ATP) of a convenient label from the relevant substrate (T. Tanabe et al, Methods in Enzymology, 1981, 71, 5–60; M. Matasuhashi, Methods in Enzymology, 1969, 14, 3–16), (ii) following the release of inorganic phosphate from ATP (P. Lanzetta et al, Anal. Biochem. 1979, 100, 95–97), or (iii) following the oxidation of NADH in a coupled assay, for example using either fatty acid synthetase or pyruvate kinase/lactate dehydrogenase enzymes. Convenient labels include carbon14, tritium, phosphorous32 or 33.

Any convenient test compound(s) or library of test compounds may be used. Particular test compounds include low molecular weight chemical compounds (molecular weight less than 1500 daltons) suitable as pharmaceutical agents for human, animal or plant use.

The enzyme of the invention, and convenient fragments thereof may be used to raise antibodies. Such antibodies have a number of uses which will be evident to the molecular biologist of ordinary skill. Such uses include (i) monitoring enzyme expression, (ii) the development of assays to measure enzyme activity and precipitation of the enzyme.

In addition we provide antisense polynucleotides specific for all or a part of an ACC1 polynucleotide of the invention.

The invention will now be illustrated but not limited by reference to the following Table, Example, References and Figures wherein:

Table 1 shows the comparative properties of native and recombinant acetyl-CoA carboxylase enzymes FIG. 1 shows a partial sequence (SEQ ID NO:1) from the *C. albicans* genome. Underlined regions were used to derive PCR primers, to generate a *C. Albicans* ACC1 specific probe.

FIG. 2 shows cloned fragments of the *C. albicans* ACC1 gene isolated from genomic DNA libraries. Arrows indicate extension of the fragment beyond the region displayed.

FIG. 3 shows sequenced XbaI-HinDIII and HinDIII subclones of clone CLS1-b1.

FIG. 4 shows the full DNA sequence (SEQ ID NO:2) of the *C. albicans* ACC1 gene. The atg start codons for Met1 and Met2 are in lower case and underlined, as is the tag stop codon.

FIG. 5 shows the full protein sequence (SEQ ID NO:3) of the *C. albicans* ACC1 gene. Putative start codons for Met1 and Met2 are shown in bold.

Figure 6:
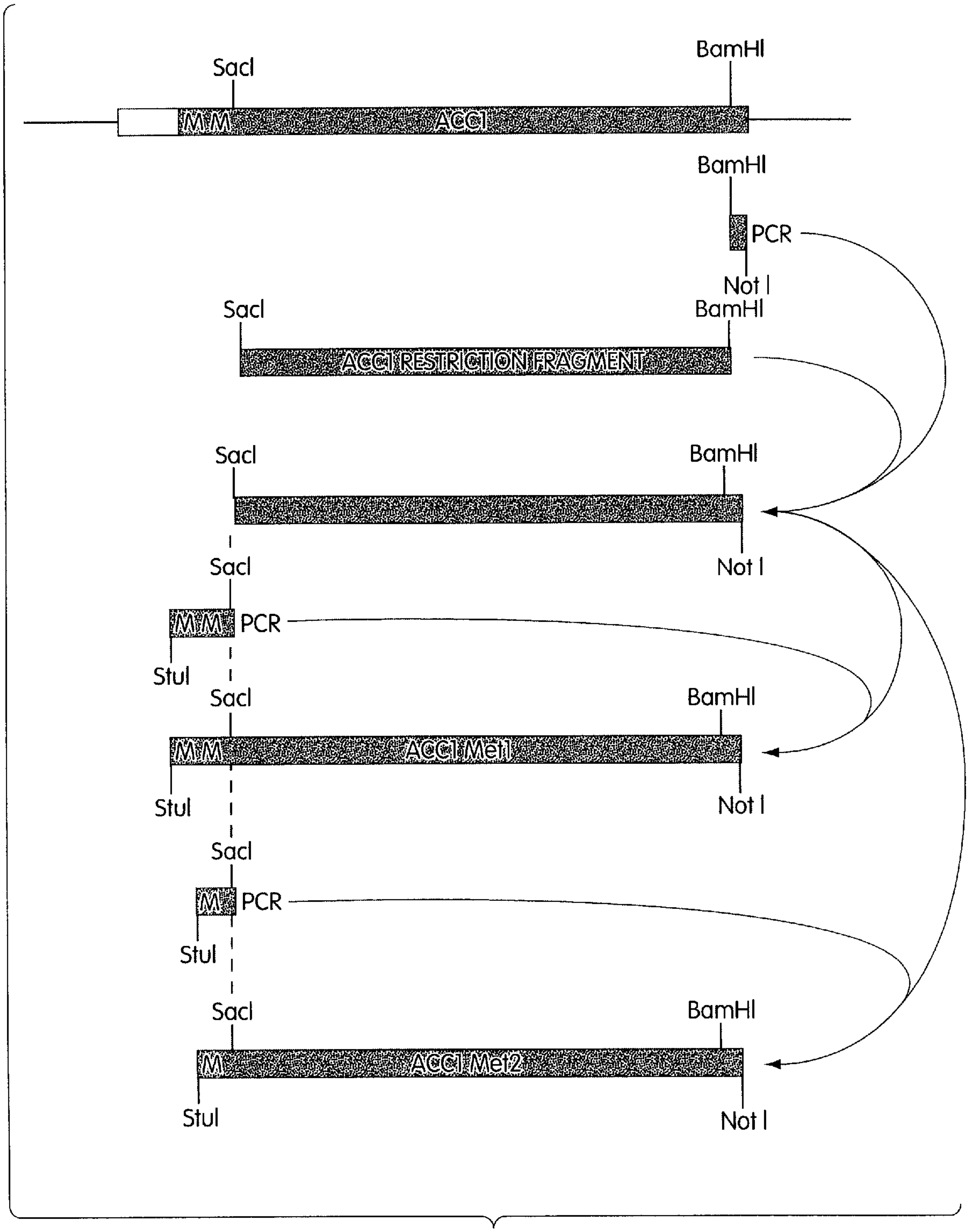

FIG. 6 shows the generation of a tailored ACC1 gene (minus promoter) for expression under control of the GAL1 promoter in plasmid pYES2. From the initial ACCase gene (line1) the core SacI-BamHI (line3) is modified by the addition of 3' BamHI-NotI (line2) and 5' StuI-SacI (different fragments for Met1 and -2 lines 5 and 7 respectively) to generate the final "portable" gene flanked by StuI-NotI (lines 6 and 8).

Figure 7:
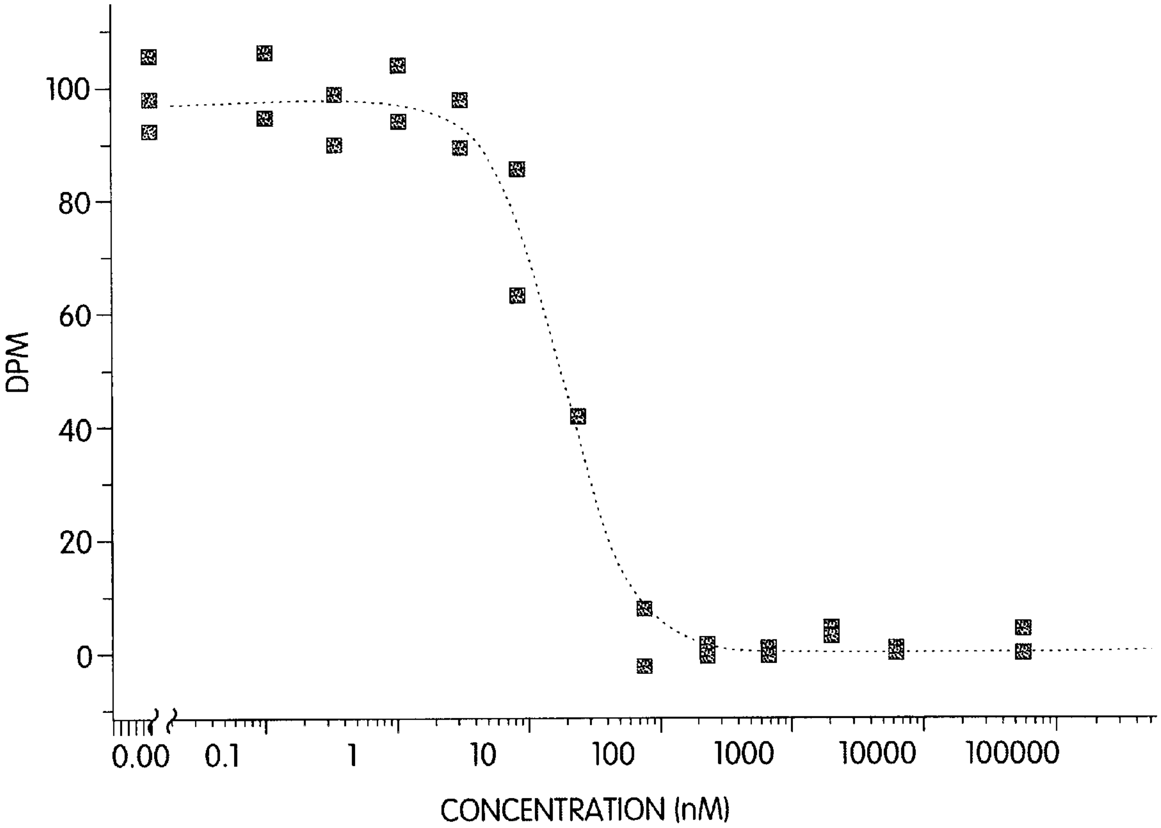

FIG. 7 shows the results of the in-vitro ACCase enzyme assay set out in the accompanying Example when Soraphen A (a specific inhibitor of the ACCase enzyme) was supplied (X-axis) over the range 0.1 nM–100 $\mu$M in the dose response regimen of the assay.

EXAMPLE 1

Cloning of the *C. albicans* ACC1 gene and generation of a heterologous *S. cerevisiae* expression system:

1) Probe Generation

We used the polymerase chain reaction (PCR) to generate a DNA probe between and including the underlined regions in FIG. 1

2) Identification of Clones from a *C. albicans* Genomic Library Hybridising to the ACCase Probe The PCR product was labelled using an "ECL direct nucleic acid labelling and detection kit" (Amersham) as described by the supplier. The PCR product (probe) was then shown to hybridise to *S. cerevisiae* (weakly) and *C. albicans* genomic DNA. in a Southern blot procedure (as described Maniatis, 1989). Two genomic DNA libraries (CLS1 and CLS2) of *C. albicans* (in the yeast-*E. coli* shuttle plasmids YEp24 and pRS316 respectively, (as described in Sherlock et al. 1994, source: Prof. John Rosamond, Manchester University) were used to isolate fragments hybridising with the probe which was radiolabelled using "Ready To Go" dCTP labelling beads (Pharmacia, as described by the manufacturer). The colony hybridisation was carried out as described by Maniatis (1989). Hybridising colonies were identified, plasmid DNA isolated, purified (Quiagen maxiprep, as described by the supplier) and sequenced (Applied Biosystems, model 377 sequencer) from their junctions with the plasmid. Several fragments carrying partial ACCase gene sequence as well as one full length clone could be identified (FIG. 2).

3) Sequencing of the Cloned Gene, Comparison with ACCases from *S. cerevisiae*, Other Fungi and Higher Eukaryotes (Plants, Mammals, Man)

The bulk of the sequence of the *C. albicans* ACC1 gene was determined (on both strands) using flanking sequence- or insert sequence-specific primers from defined HinDIII and XbaI-HinDIII subfragments (of clone CLS1-b1) cloned into pUC19 (see FIG. 4). The promoter and 5' coding region absent from this clone was established from CLS2-d1 and the gene's 3' end from CLS2-13 using insert specific primers. All junctions including the ones between the HinDIII subfragments were verified from the full length clone CLS2-13 (in Yep24. The full length DNA sequence of *C. albicans* (Ca) ACC1 is shown in FIG. 5*a* and the protein translation in FIG. 5*b*. The two potential start Methionines, Met1 and Met2 are shown in bold The protein is homologous to ACCases of other fungi (*S. cerevisiae, S. pombe* and *U maydis*) and also to the plant (*Brassica napus*), mammalian (sheep, chicken and rat) and human enzymes. Of the two potential start codons of *C. albicans* ACC1, Met 2 seems the more likely one as the sequence between Met1 and Met2 is unrelated to the other ACCases and indeed to any other protein sequence in the EMBL/Genbank database. The high degree of homology between ACCases of different species and the apparent lack of an identifiable fungal subgroup makes it even more important to use the actual target enzyme (here from the pathogen *C. albicans*) as a screening tool to identify specific inhibitors.

4) Generation of a Heterozygous ACC1 Deletion Strain of *S. cerevisiae*

As ACCase is an essential enzyme, only one allele of a diploid cell can be deleted without loss of survival. One ACC1 gene of a diploid *S. cerevisiae* strain (JK9-3Daa, Kunz et al. 1993) was therefore disrupted using the kanamycin resistance cassette as described by Wach et al. using the protocol described therein. Sporulation of the heterozygous diploid (ACC1/acc1::KANMx) yields only two viable spores (which are kanamycin-sensitive) showing the essentiality of the ACC1 gene as well as the characteristic arrest phenotype for the two inviable spores (as published by Hallacher et al., 1993).

5) Complementation of a *S. cerevisiae* ACC1 Deletion with the Cloned Candida Gene, Ca ACC1

The heterozygous ACC1/acc1::KANMx strain was transformed with one full length *C. albicans* gene (CLS2-13 in Yep24). Expression of the gene from this plasmid will be due to functionality of the Candida ACC1 promoter in the heterologous *S. cerevisiae* system. Complementation of the knockout was demonstrated by sporulating the diploid transformants. In most cases 3–4 viable (haploid) spores were detected. The analysis of tetrads indicated that kanamycin-resistant colonies were only formed if they also contained the complementing CLS2-13 plasmid, as indicated by the presence of the URA3 transformation marker. This clearly shows that the *C. albicans* gene fully complements the ACCase function in *S. cerevisiae*. Therefore the strain generated can be used to screen for inhibitors which are specific for the Candida enzyme in the absence of a background of Saccharomyces enzyme. As demonstrated by its functionality, the heterologous protein folds correctly in the host, *S. cerevisiae*, where it must also have been correctly biotinylated by the *S. cerevisiae* machinery (carried out by ACC2, encoding protein-biotin-ligase).

To facilititate purification of *C. albicans* ACCase, it is beneficial to achieve overexpression of the protein in a suitable host. Therefore the *C. albicans* promoter was replaced by the stronger and inducible *S. cerevisiae* GAL1 promoter. As the Candida sequence had revealed two potential start codons (see FIG. 4) for the ACC1 reading frame, both versions were placed under GAL1 control. To generate appropriate restriction sites for cloning, the ACC1 gene was modified via PCR at both ends (see FIG. 6 above). and cloned into plasmid pYES2 (Invitrogen) as a StuI-NotI fragment into HinDIII (fill-in)-NotI sites of the vector. The identity of the PCR-modified gene-parts with the original ones was confirmed by sequencing. Both constructs (Met1 and Met2) complement the *S. cerevisiae* ACC1 knockout when the cells are grown on galactose but not on glucose (where the GAL1 promoter is switched off). Growth is very poor if the gene is transcribed initiating at Met1, whereas Met2 restores wild type growth rates in S.cerevisiae.

6) Overexpression of the Ca ACCase to Facilitate Protein Purification and use for Screening Purposes Materials Growth Media:

Sabouraud Dextrose broth

Yeast peptone dextrose broth (YPD)

Yeast peptone galactose broth (YPGal) (i.e. 2% w/v galactose)

Growth of Cells

*Candida albicans* B2630 (Janssen Pharmaceutica, Beerse, Belgium) was maintained on Sabouraud dextrose agar slopes at 37° C. which were subcultured biweekly. For the growth of liquid cultures for experiments, *C. albicans* grown on Sabourauds dextrose agar for 48 h at 37° C. was used to inoculate 50 ml Sabouraud dextrose broth containing 500 μg/l d-biotin. This was incubated for 16 h at 37° C. on a platform shaker (150 rpm). 1.5 ml of this culture was added to each of 24×2 litre conical flasks, each containing 1 litre of Sabouraud dextrose broth containing 500 μg/l d-biotin, giving a final inoculum concentration of approximately $1.5\times10^6$ cfu $ml^{-1}$. The cultures were grown for 9 h, at 37° C. (log phase) with shaking (150 rpm). Cell numbers in liquid culture were determined spectrophotometrically (Philips PU8630 UV/VIS/NIR Spectrophotometer) at 540 nm in a 1 cm path length cuvette. Absorbance was linearly related to cell number up to an OD. of 2.0.

*Saccharomyces cerevisiae* strains Mey 134 and CLS2-13 were maintained on Yeast peptone dextrose (YPD) agar plates at 30° C., which were subcultured biweekly. For the growth of liquid cultures for experiments, the *S. cerevisiae* strains were grown on YPD agar for 48 h at 30° C. and were then used to inoculate 50 ml YPD broth containing 500 μg/l d-biotin, which was incubated at 30° C. for 16h on a platform shaker (200 rpm). 2.0 ml of this culture (approx. $4\times10^8$ cfu/ml) was added to each of 24×2 litre conical flasks, each containing 1 litre of YPD broth containing 500 μg/l d-biotin, giving a final inoculum concentration of approximately $8\times10^5$ cfu/ml. The cultures were grown for 9 h, at 30° C. (log phase) with shaking (200 rpm). Cell numbers in liquid culture were determined spectrophotometrically (Philips PU8630 UV/VIS/NIR Spectrophotometer) at 540 nm in a 1 cm path length cuvette.

*Saccharomyces cerevisiae* strains PNS117a 5C, PNS117b 6A, and PNS120a 6C were maintained on Yeast peptone galactose (YPGal) agar plates at 30° C. which were subcultured biweekly. For the growth of liquid cultures for experiments, the *S. cerevisiae* strains were grown on YPGal agar for 48 h at 30° C. and were then used to inoculate 50 ml YPGal broth containing 500 μg/l d-biotin and 200 μg/ml kanomycin, which were incubated at 30° C. for 30h on a platform shaker (200 rpm). 2.0 ml of this culture (approx. $4\times10^8$ cfu/ml) was added to each of 24×2 litre conical flasks, each containing 1 litre of YPGal broth containing 500 μg/l d-biotin and 200 μg/ml kanomycin, giving a final inoculum concentration of approximately $8\times10^5$ cfu/ml. The cultures were grown for approximately 23h at 30° C. (log phase) with shaking (200 rpm).

Determination of Cell Number

Cell numbers were determined using a standard viable count agar based plating method, using the appropriate agar media.

Preparation of Fungal ACCase Enzyme

Cultures of the appropriate yeast strains were grown to the exponential phase of growth (for Saccharomyces and Candida strains respectively). These were then harvested by centrifugation (4400 g, 10 min, 4° C.), washed twice in 700 ml of 50 mM Tris pH7.5 containing 20% w/v gylcerol, resuspending the cell pellet each time. The final washed pellet was fully resuspended into a thick slurry using 10 to 20ml of buffer (50 mM Tris pH7.5 containing 1 mM EGTA, 1 mM EDTA (disodium salt), 1 mM DTT, 0.25mM Pefabloc hydrochloride, 1 μM Leupeptin hemisulphate, 1 μM Pepstatin A, 0.5 μM Trypsin inhibitor and 20% w/v glycerol). The volume of buffer required was dependent on the total packed cell wet weight. (i.e. 1 ml buffer added per 6 gm of packed wet cell pellet).

The cell paste was homogenised using a pre-cooled Bead-Beater (Biospec Products, Bartlesville, Okla. 74005) with 4×10 second Bursts, allowing 20 second intervals on ice. The preparation was then centrifuged at 31,180 g for 30 minutes. After centrifugation the supernatant was immediately decanted into a container, then aliquoted before snap freezing in liquid nitrogen. The preparation was then stored at −80° C. and was found to be stable for at least 2 months.

All enzyme preparation steps were carried out at +4° C., unless otherwise stated.

In-vitro ACCase Assay

The assay was conducted in 96 well, flat bottomed polystyrene microtitre plates. All test and control samples were tested in duplicate in this assay.

100 μl of the ACCase enzyme preparation (in 50 mM Tris pH7.5 containing 1 mM EGTA, 1 mM EDTA (disodium salt), 1 mM DTT, 0.25 mM Pefabloc hydrochloride, 1 μM Leupeptin hemisulphate, 1 μM Pepstatin A, 0.5 μM Trypsin inhibitor, and 20% w/v glycerol) was added to each well of the microtitre plate. Each well contained either a 3 μl test sample made up in DMSO or 3 μl DMSO alone (NB. Final DMSO concentrations in the assay were 1.48% v/v). The microtitre plates were placed in a water bath maintained at 37° C. 10 μl of [$^{14}$C] $NaHCO_3$ containing 9.25 kBq in 378 mM $NaHCO_3$ was then added to each well. The reaction was initiated by the addition of 100 μl of Acetyl Coenzyme A containing assay buffer (50 mM Tris pH7.5 containing 4.41 mM ATP(disodium salt), 2.1 mM Acetyl Coenzyme A, 2.52 mM DTT, 10.5 mM $MgCl_2$, and 0.21% w/v Albumin [Bovine, fraction V]), (removed from ice 5 minutes before use) to each well. The tubes were incubated at 37° C. for 5 minutes. The reaction was then terminated by the addition of 50 μl of 6M HCl to each well. In parallel, a pre-stopped assay control was set up which involved adding the 50 μl of 6M HCl prior to [$^{4}$C] $NaHCO_3$ and the assay buffer (No further HCl additions were made to these wells after the 5 minute incubation). The DPM values for the pre-stopped assay were subtracted from the normal assay situation.

After the addition of the stop reagent the plates were left open in the water bath for a further 30 minutes to allow the $^{14}CO_2$ to escape. After this time 150 μl of each reaction mixture were applied onto individual GF/C glass microfibre filter discs and allowed to dry thoroughly before adding scintillation fluid. Radioactivity in the samples was then determined by scintillation counting (Wallac WinSpectral 1414, Turku, Finland).

IC50's were calculated from the data using non-linear regression techniques available in the ORIGIN software package (Microcal Software Inc., Massachusetts, USA). Soraphen A which is a specific inhibitor of ACCase was supplied over the range 0.1 nM-100 μM in the dose response regimen of the assay.

Protein Determination

The total protein concentration of each ACCase preparation used was determined by the Coomasie Blue method (Pierce, Ill., USA), (using 1 cm path length cuvettes read 595 nm (Philips PU8630 UV/VIS/NIR Spectrophotometer).

In-vitro Antifungal Activity

Compounds were tested over a concentration range of 1024–0.00098 μg/ml by a broth-dilution method in microtitre plates using doubling dilutions in YPD or YPGal (both containing 500 μg/l d-biotin). Stock solutions of inhibitors were prepared at 51.2 mg/ml in Dimethyl sulphoxide (DMSO) (final assay concentration of DMSO was 2% v/v). Each Yeast culture was added to the well to give a final $10^4$ cfu/well. The plates were incubated at 30° C. for 48h and MIC's determined visually.

Discussion

Expression of ACCase, a biotinylated protein, was monitored by a "biotin-avidin affinity western blot" as described by Hal3lacher et al., 1993. Expression of the *C. albicans* ACC1 gene from its own promoter from plasmid Yep24 was comparable to that of the *S. cerevisiae* gene (no overexpression). Expression under control of the GAL1 promoter however, was considerably higher indicating a drastically increased level of biotinylated and therefore fully functional enzyme. Transcription of the gene was fully induced as the cells had to be grown on galactose to be viable. On glucose the GAL1 promoter is completely off, causing the cells to arrest and eventually die due to insufficient supply of ACCase). The *S. cerevisiae* strain described in this application is a convenient source of the *C. albicans* enzyme. The engineered strain possesses no residual background ACCase because the gene coding for the *S. cerevisiae* enzyme had been removed. Congenic versions of such a strain (genetically identical apart from the ACCase gene carried) expressing different ACCases (e.g. the different human (Abu-Elheiga et al. 1995), mammalian (Lopez-Casillas et al., 1988, Takai et al. 1988, Barber et al., 1995)), plant (Schulte et al., 1994) or other fitmgal enzymes (Al-Feel et al., 1992, Saito et al., 1996, Bailey et al., 1995)) can be used as tools for screening. Differences in growth of such strains may be solely dependent on differences in their ACCase activity. Differential growth in the presence of ACCase inhibitors (for example soraphenA or compounds yet to be identified) indicates selectivity of the drug towards one type of the ACCase enzyme.

References

Abu-Elheiga L., Jayakumar A., Baldini A., Chirala S. S., Wakil S. J.; Proc. Natl. Acad. Sci. U.S.A. 92: 4011–4015 (1995).

Al-Feel W., Chirala S. S., Wakil S. J.; Proc. Natl. Acad. Sci. U.S.A. 89:4534–4538(1992). Bailey A. M., Keon J. P. R., Owen J., Hargreaves J. A.; Mol. Gen. Genet. 249:191–201(1995). Barber M. C., Travers M. T.; Gene 154:271–275(1995). Haβlacher M., Ivessa A. S., Paltauf F., Kohlwein S. D.; J. Biol. Chem. 268:10946–10952 (1988).

Ito, H., Fukuda, Y., Murata, K., Kimura, A.; J. Bacteriol. 153: 163–168 (1983)

Kunz. J., Henriquez, R., Schneider, U., Deuter-Reinhard, M., Movva, N. R., Hall, M. N.; Cell 73: 585–596 (1993)

Lopez-Casillas F., Bai D.-H., Luo X., Kong I.-S., Hermodson M. A., Kim K.-H.; Proc. Natl. Acad. Sci. U.S.A. 85:5784–5788(1988).

Maniatis T., Frisch E. F., Sambrook J.; Molecular Cloning, Cold Spring Harbour Laboratory Press (1989)

Saiki R. K., Gelfand D. H., Stoffel S., Sharf S. J., Higuchi R., Hom G. T., Mullis K. B., Erlich H. A.; Science 239: 487–494 (1988)

Saito A., Kazuta Y., Toh H., Kondo H., Tanabe T.; S. pombe ACC1, Submitted (Dec-1996) to Embl/Genbank/Ddbj Data Banks.

Schulte W., Schell J., Toepfer R.; Plant Physiol. 106:793–794(1994).

Sherlock G., Bahman A. M., Mahal A., Shieh J. C., Fewrreira M., Rosamond J.; Mol. Gen. Genet. 245: 716–723.

Takai T., Yokoyama C., Wada K., Tanabe T.; J. Biol. Chem. 263:2651–2657(1988). Wach A., Brachat A., Poehlmann R., Philippseen P.; Yeast 10: 1793–1808 (1994)

TABLE 1

Comparative properties of native and recombinant acetyl-CoA carboxylase enzymes

| Yeast strain | Cell doubling time (minutes) | Growth temperature for ACCase preparation (° C.) | Liquid MIC (μg/ml) for Soraphen A | IC50 for Soraphen A (nM) against ACCase preparations | Specific activity of ACCase preparation (nmoles product/ min/mg protein) |
|---|---|---|---|---|---|
| *C. albicans* B2630 | 56 | 37 | 0.003 | | |
| *S. cerevisiae* Mey 134 | 160 | 30 | 8 | | 0.641 |
| *S. cerevisiae* CLS2-13 | 163 | 30 | 2 | 2.499 | 3.054 |
| *S. cerevisiae* PNS 117a 5C | 253 | 30 | 2 | 17.518 | 7.025 |
| *S. cerevisiae* PNS 117b 6A | 222 | 30 | 4 | 13.083 | 10.573 |
| *S. cerevisiae* PNS 120a 6C | 303 | 30 | 0.5 | ND | 0.244 |
| *S. cerevisiae* PNS 120b 1C | 287 | 30 | 0.125 | ND | ND |

Key: ND = not determined

What is claimed is:

1. An isolated polynucleotide encoding an Acetyl-COA-carboxylase (ACCase) polypeptide defined by SEQ ID NO:3 or amino acid residues 46-2270 of SEQ ID NO: 3, from *Candida albicans.*

2. An isolated polynucleotide as claimed in claim 1 and as set out in SEQ ID NO: 2.

3. An isolated polynucleotide as claimed in claim 2, characterized in that the sequence starts at base number 1173 with the start codon atg2 as set out in SEQ ID NO: 2.

4. An isolated polynucleotide which comprises nucleotides 1038 to 7847 of SEQ ID NO:2 and is further flanked by Stu1 (5'-end)-Not1 (3'-end) restriction sites.

5. An isolated polynucleotide which comprises nucleotides 1173 to 7847 of SEQ ID NO:2 and is further flanked by Stu1 (5'-end)-Not1 (3'-end) restriction sites.

6. An isolated or purified Acetly-COA-carboxylase (ACCase) polypeptide encoded by the polynucleotide of claim 1.

7. An isolate polynucleotide probe comprising a polynucleotide as claimed in any one of claims 1, 2, 3, 4 and 5.

8. An Acetyl-COA-carboxylase (ACCase) polypeptide from *Candida albicans* in isolated and purified form defined by SEQ ID NO:3 or amino acid residues 46-2270 of SEQ ID NO:3 from *Candida albicans.*

9. A polypeptide as claimed in claim 8, characterized in that the sequence starts at amino acid number 46 with Met2 as set out in SEQ ID NO: 3.

10. A polypeptide as claimed in claim 8 and obtained by expression of a polynucleotide as claimed in any one of claims 1, 2, 3, 9 and 5.

11. An isolated RNA transcript corresponding to a polynucleotide as claimed in any one of claims 1, 2, 3, 9 and 5.

12. An expression system for expression of an Acetyl-COA-carboxylase (ACCase) polypeptide from *Candida albicans*, which system comprises an *S. cerevisiae* host strain having a *Candida albicans* ACCase-encoding polynucleotide as claimed in any one of claims 1–3 inserted in place of the native ACCase-encoding gene from *S. Cerevisiae*, whereby the *Candida albicans* ACC1 polypeptide is expressed.

13. An expression system as claimed in claim 11, wherein the ACCase polypeptide is expressed using a promoter heterologous with respect to the natural promoter for ACCase in *Candida albicans.*

14. An expression system as claimed in claim 13, and used to provide an Acetyl-COA-carboxylase (ACCase) polypeptide from *Candida albicans* in sufficient quantity and with sufficient activity for compound screening purposes.

15. Use of an cetyl-COA-carboxylase (ACCase) polypeptide from *Candida albicans* as claimed in claim 8 in an assay to identify inhibitors of the polypeptide, wherein said assay comprises:

(i) isolating an ACCase enzyme preparation comprising the polypeptide of claim 6;

(ii) incubating said ACCase enzyme preparation in the presence of a test sample; and (iii) measuring the degree of inhibition of the ACCase enzyme preparation by the test sample.

16. Use as claimed in claim 15 in pharmaceutical research. polypeptide from Candida albicans.

17. An expression system as claimed in claim 13, wherein the heterologous promoter is *Saccharomyces cerevisiae* GAL1.

18. A method of identifying inhibitors of an enzyme activity of an Acetyl-COA-carboxylase (ACCase) polypeptide from *Candida albicans*, comprising (i) isolating an Acetyl-COA-carboxylase (ACCase) polypeptide;

(ii) contacting said Acetyl-COA-carboxylase (ACCase) polypeptide with a test sample; and (iii) measuring the degree of inhibition of the enzyme activity of said Acetyl-COA-carboxylase (ACCase) polypeptide in the presence of the test sample.

19. The method of claim 18, wherein said method is conducted as part of pharmaceutical research.

* * * * *

UNITED STATES PATENT AND TRADEMARK OFFICE

CERTIFICATE OF CORRECTION

PATENT NO. : 6,566,048 B1
DATED : May 20, 2003
INVENTOR(S) : Graham K. Dixon et al.

It is certified that error appears in the above-identified patent and that said Letters Patent is hereby corrected as shown below:

Column 1,
Line 44, replace "underlined at codons" with -- underlined atg codons --.
Line 52, replace "unique Stu1" with -- unique StuI --.

Column 3,
Line 52, replace "C. Albicans" with -- C. albicans --.

Column 5,
Line 19, replace "Hallacher" with -- Haβlacher --.

Column 7,
Line 15, replace "In-vitro ACCase Assay" with -- In-vitro ACCase Enzyme Assay --.
Line 39, replace "prior to [$^{4}$C]" with -- prior to [$^{14}$C] --.

Column 8,
Line 8, replace "by HaI3lacher et al." with -- by Haβlacher et al. --.
Line 26, replace "fitmgal" with -- fungal --.
Line 55, replace "Hom G. T.," with -- Horn G.T., --.

Column 28,
Line 66, replace "An isolate" with -- An isolated --.

Column 29,
Lines 9 and 11, replace "claims 1, 2, 3, 9 and 5" with -- claims 1, 2, 3, 4, and 5 --.
Line 19, replace "claim 11" with -- claim 12 --.
Line 27, replace "cetyl-COA" with -- Acetyl-COA --.

UNITED STATES PATENT AND TRADEMARK OFFICE

CERTIFICATE OF CORRECTION

PATENT NO. : 6,566,048 B1
DATED : May 20, 2003
INVENTOR(S) : Graham K. Dixon et al.

It is certified that error appears in the above-identified patent and that said Letters Patent is hereby corrected as shown below:

Column 30,
Line 2, replace "claim 6" with -- claim 8 --.
Line 10, delete "polypeptide from Candida albicans."
Line 19, after "polypeptide" add -- of claim 6 --.

Signed and Sealed this

Ninth Day of September, 2003

JAMES E. ROGAN
*Director of the United States Patent and Trademark Office*

SEQUENCE LISTING

<160> NUMBER OF SEQ ID NOS: 3

<210> SEQ ID NO 1
<211> LENGTH: 523
<212> TYPE: DNA
<213> ORGANISM: Candida albicans

<400> SEQUENCE: 1

```
gcacgcttga cggttttcac caaatgcgaa aatatgacca aattgagaat ccgaaaatga     60

atggatagaa gattggttac caactgagaa ataaccccac acattagaag aagaacggaa    120

attcaattca tgtaaagaac caccacttgg tttaaaacct tcaccaggat cttcagaagt    180

aatacgacaa gcagtacaat gtccctttgg tgttggtctt ctttgactaa ccaatgaagt    240

ttctgacttg aattcaaaat caatatcagt agtggtatga ggatcggcac cgcacaaagt    300

tctgatatct ctgattctat gcattggtat acccatagca atttgtaatt gagcagctgg    360

taaattaaca cctgtcacca tttcagtggt tggatgttca acttgcaatc ttgggttcaa    420

ttccaaaaag tagaatttat cttcagcgtg gggagtaaag gtactcaaca gtaccagggg    480

gttacataac caacttattt tacccaatct gactggtgga ttt                      523
```

<210> SEQ ID NO 2
<211> LENGTH: 8054
<212> TYPE: DNA
<213> ORGANISM: Candida albicans

<400> SEQUENCE: 2

```
aatatattgc ttccttttga taggaagtaa ctccgagtgt ttgaatttga tatatgttat     60

tcatatacgt tcaatggctc tcttctatgc tttgtatata ctttcttttg aatagatact    120

catgtaaaga gatttgaaac catattctaa ccaacaaaaa tattgtacgg tataggttag    180

aaaaaaaact ccgtaaggtc cgcttacacg gttaaattga aaacacgtta aaaatatatt    240
```

-continued

```
tgggtaatgg actaagctat atacagtact caacaaaaat gaaatcaaac acaatgttct    300
ttgggaaatt catttcatgc aactagggtg attctctttc tactatccaa caacgataac    360
cctgcttttg aaaaatcttt tctaaattca aattgatata attcttattt atatattact    420
ttctttttcc catataaccc catttttttt ttggaatcat atttgttttt gatttttgct    480
ttccctttca gtctgaggaa catactaatt acgaacaaca attatacatc caatcttcat    540
ctaacgaatt gattatttac atttattaaa cccttggata caaactgatt acacttttta    600
gttagtttgt tcaattataa gggtattata caacaaagat atcatttaaa gttaaatctc    660
aatctggaat aataaaagta ttcaacactt ttgcttacaa taggtatgtt caaaatcaat    720
tgaagccatc gagataagaa attaagcaaa aacgtttaca attgttgtgt gtgtgttgca    780
gtgtttgaag aagctcgagt gattgctttt cttcggcatc agctgtgttg ggaacatctt    840
gtcgttaaag tttcggagta atattagagt aatggaacga aaaaaacaaa ataaagttct    900
ggaaccacaa agatttgaaa aattgggtag aaacaaaaaa aagacaaagc aggaacccaa    960
caataaatga ataaacactc aaaaactact cacaacaaca acacttattt tcacttgctt   1020
tatttcttcg atttttatg agatgcaaat tatctctaat aaagaatact aactcacttg    1080
tacatagatc gcgtttccta attacaaaac cacaactata tatacctcat cgtcattata   1140
tcccattcaa gaacatattc aagtcattgt taatgtcaga tcaatctcca tctcctagtc   1200
ctagcgattc ccttagctac actacattac atgaaaattt gccatctcat ttcttgggtg   1260
gaaattcagt tttgaatgct gaaccttcta aagtcagaga ctttgtcaga gctcatcaag   1320
gtcatacagt tatttcgaaa attttaattg ccaacaatgg tatagctgca gttaaagaaa   1380
tcagatcagt tagaaaatgg gcttatgaaa catttggtga cgaaaaagcc atacagttta   1440
ccgttatggc cactccagaa gatttggaag ctaatgccga atatattaga atggccgacc   1500
aattcattga agtccctggt ggcaccaata acaataacta tgctaatgtt gatctcattg   1560
tagagatagc agaaagtaca aatgctcatg ccgtttgggc tgggtggggg catgcttcag   1620
agaatccttt gttaccagaa aaattagctg catctcccaa aaaaattatt tttattggtc   1680
ctcctggttc agctatgaga tctttaggtg acaagatttc atctactata gttgctcaac   1740
atgctcaagt accatgtatt ccatggtccg gtactggtgt tgatgaagtg aaaatagacc   1800
cacaaactaa tttggtttct gttgctgatg atatttatgc caaagggtgc tgtactagtc   1860
cagaagatgg tttagaaaaa gccaaaaaaa ttgggttccc agttatgatt aaagcctctg   1920
aaggtggtgg tggtaaaggt attagaaaag ttgatgatga gaaaaacttc attaccttat   1980
acaaccaagc agctaatgaa ataccaggtt ctcctatctt tattatgaag ttagcaggtg   2040
atgccagaca tttagaagtt caattactag cagatcaata cggtactaac atttcccttt   2100
ttggaagaga ttgttccgta caaagaagac accaaaagat tattgaagaa gcaccagtca   2160
ccattgccag aaaggaaact ttccacgaaa tggaaaatgc agcagtcaga ttgggtaaat   2220
tagttggtta tgtatccgct ggtactgttg agtatcttta ctcccacgct gaagataaat   2280
tctacttttt ggaattgaac ccaagattgc aagttgaaca tccaaccact gaaatggtga   2340
caggtgttaa tttaccagct gctcaattac aaattgctat gggtatacca atgcatagaa   2400
tcagagatat cagaactttg tacggtgccg atcctcatac cactactgat attgattttg   2460
aattcaagtc agaaacttca ttggttagtc aaagaagacc aacaccaaag ggacattgta   2520
ctgcttgtcg tattacttct gaagatcctg gtgaaggttt taaaccaagt ggtggttctt   2580
tacatgaatt gaatttccgt tcttcttcta atgtgtgggg ttatttctca gttggtaacc   2640
```

-continued

```
aatcttctat ccattcattt tcggattctc aatttggtca tattttcgca tttggtgaaa   2700
accgtcaagc ttcaagaaaa catatggttg ttgccttgaa agaattgagt attagaggtg   2760
attttagaac tactgttgag tatttaatca aattgttaga aactccagat ttcgaggata   2820
ataccattac aactggttgg ttggatgaat taatcaccaa aaagttgact gctgaaagac   2880
cagatccaat agttgctgtt gtttgtggag ctgtaaccaa agcacacatc caggctgagg   2940
aagagaaaaa ggaatacatc caatctttgg aaaaaggtca agttcctcac agaaacttat   3000
tgaaaactat tttcccagtt gagtttattt atgaaggtga aagatacaag ttcactgcta   3060
ctaaatcttc agaagataaa tatactttgt tccttaatgg ttctcgttgt gttgttggtg   3120
cacgttcatt gtccgatggt ggtttattgt gtgcattaga tgggaaatca cattctgtct   3180
attggaagga agaggcatct gccactagat tatcagttga tggcaaaact tgtttattag   3240
aagttgaaaa tgatccaaca caattaagaa ctccatctcc aggtaaattg gtcaagtatt   3300
tggttgacag tggtgaacat gttgatgctg gtcaaccata cgctgaagtc gaagttatga   3360
aaatgtgtat gcctttgatt gctcaagaaa atggggtagt gcagttgatt aaacaaccgg   3420
gttccacagt taatgctggt gatatcttgg ccattttggc attggacgat ccatctaagg   3480
tcaaacatgc taaaccattt gaaggtactt taccatctat gggtgagcca aatgttacag   3540
gtactaaacc agcacataaa ttcaatcatt gtgctggtat tttgaaaaac attttggctg   3600
gttatgataa tcaagtgatt ttgaattcta ctttaaagag tcttggtgaa gttttgaaag   3660
acaatgaatt gccatactct gaatggcaac aacaaatttc agctttacac tccagattgc   3720
cacctaaatt ggatgacgga ttgactgcat tggttgaaag aactcaaagt agaggtgctg   3780
aattccctgc tcgtcaaatt ttaaaactca tcaccaaatc aattgctgaa aatggtaatg   3840
atatgttaga agatgttgtt gcaccattgg tttctattgc cacaagttac cagaatggtt   3900
tggttgaaca cgaatacgat tactttgcat ctttgattaa cgaatattat gacgttgaaa   3960
gtttgttttc aggtgaaaat gttagagaag ataatgttat cttgaaatta agagatgaaa   4020
acaaatctga tttgaaaaaa gttattggta ttggtttgtc tcattcacgt gttagtgcca   4080
agaacaattt gattttagct attttggaca tttatgaacc attgttgcaa tccaactcgt   4140
cagttgctgc ctctatcaga gaagctttaa agaacttgtt cattagacct cgtgcttgtg   4200
ccaaagttgc attaaaggca agagaaattt taattcaatg ttctttacct tccatcaagg   4260
aaagatccga tcaattggaa catattttga ggtcatctgt tgttcaaacc tcttatggtg   4320
aaatttttgc taaacataga gaaccaaatt tggaaattat tcgtgaggtt gttgattcca   4380
aacatattgt ttttgatgtg ttggcacaat tcttaatcaa tccagaccca tgggttgcca   4440
ttgctgccgc tgaagtttat gtcagacgtt cataccgtgc ttatgatttg ggtaaaattg   4500
aatatcatgt taatgacaga cttcctattg ttgaatggaa attcaagttg gctaatatgg   4560
gagccgctgg tgtaaacgat gctcaacagg ctgctgctgc cggtggcgat gattcgacat   4620
ctatgaaaca tgcagcttct gtgtctgatt tgacctttgt tgttgattct aaaaccgagc   4680
attccacaag aactggtgtt ttagctccag caagacactt ggatgatgtt gatgaaactc   4740
ttacagctgc attggaacaa ttccaaccag ccgatgctat ttcatttaaa gcaaagggtg   4800
aaactccaga gttattaaat gttttgaata ttgtcattac cagtattgat ggttactccg   4860
atgaaaatga atacttgagc agaattaatg aaatcttgtg cgaatacaaa gaagagttga   4920
tttctgctgg tgttcgtcgt gttacatttg tttttgctca tcaaattggt caatatccta   4980
```

-continued

```
aatattatac ttttactggt cctgactatg aagaaaacaa ggttattaga cacattgaac   5040
cagctttggc tttccaattg gaattgggaa gattagccaa tttcgatatc aaaccaattt   5100
tcactaacaa cagaaacatc catgtatatg atgcaattgg gaagaatgct ccttctgata   5160
aaagattttt caccagaggg attattagaa ccggtgttct taaagaagac attagcatta   5220
gtgaatattt gattgctgaa tccaacagat taatgaatga tattttggat actttagaag   5280
ttattgacac ttctaattct gatttaaacc atattttcat taacttttcc aatgctttca   5340
atgttcaagc ttcagatgtt gaggctgcct ttggatcatt cttagaaaga tttggtagaa   5400
gattatggag attaagagtt actggtgctg aaattagaat tgtctgtact gatcctcaag   5460
gtacttcgtt cccattgcgt gctatcatta ataatgtttc tggttatgtt gtcaaatcag   5520
aattgtattt ggaagtgaaa aatcctaaag gtgaatgggt tttcaaatcc attggtcatc   5580
ctggttccat gcatttgaga cctatctcaa ctccatatcc agttaaagaa tctttacaac   5640
caaaacgtta caaggctcac aatatgggta ccacttatgt gtatgacttc ccagaattgt   5700
ttcgtcaagc aacaatttca caatggaaaa aatatggcaa aaaagtacca aaagatgttt   5760
tcgtgtcttt agaattgatc actgatgaaa ctgattcctt aatagctgtt gaaagagatc   5820
cgggtgctaa caaaattgga atggttggat tcaaagtcac tgctaaaact cctgaatacc   5880
ctcatggtcg tcaattaatt attgttgcca atgatatcac ccacaagatt ggttcttttg   5940
gtccagaaga agataattat ttcaacaagt gtactgaatt ggccagaaaa ttaggtattc   6000
caagaattta cctttctgca aattcaggtg ctagaattgg tgttgctgag gaattgattc   6060
cattatacca agttgcctgg aatgaagaag ggtctcctga caaaggattc agatacttgt   6120
acttgagtac tgctgctaaa gagtctttag aaaaagatgg taaaagtgac agtgttgtta   6180
ctgaacgtat tgttgaaaaa ggtgaagagc gtcatgtcat taaagctatt attggtgccg   6240
aagatggctt aggggttgaa tgtcttaaag gatcaggttt aattgctggt gccacatcaa   6300
gagcttacaa ggatatattt accatcactt tggtaacttg tagatctgtt ggtattggtg   6360
cttatttggt tagattgggt caaagagcca ttcaaatcga tggtcaacct attattttaa   6420
ctggtgctcc tgctatcaat aaattgttgg gtagagaagt gtattcttcc aatcttcaat   6480
tgggtggtac tcaaatcatg tacaataatg gtgtttctca tttgacagct aatgatgatt   6540
tggctggggt tgaaaaaatt atggaatggt tatcatatgt tccagctaaa cgtggtttac   6600
cagtgccaat tttggaatca gaagattctt gggacagaga tgttgattac tacccaccaa   6660
aacaagaagc ttttgatgtt agatggatga tccaaggtag agaagttgat ggtgaatatg   6720
aatctgggtt atttgataaa gattcattcc aagaaacatt atctggttgg gctaaaggtg   6780
ttgttgttgg tagagcacgt ttgggtggta ttccaattgg tgttattggt gtcgaaacca   6840
gaacagtgga aaacttgatt cctgctgatc cagcaaatcc agactctaca gaaagtttga   6900
ttcaagaagc aggtcaagtg tggtatccta actctgcttt taagacagca caagctataa   6960
atgatttcaa caatggtgaa caattgccat taatgatttt agcaaattgg agaggtttct   7020
ctggtggtca aagagatatg tacaatgaag tcttgaaata tggttcattt attgttgatg   7080
ctttagttga cttcaagcaa cctatcttca cttacattcc accaaatgga gaattgagag   7140
gtggctcttg ggttgttgtt gatccaacca tcaactcaga tatgatggaa atgtatgccg   7200
atgtcgattc gagagctggt gttttggaac cagaaggtat ggttggtatc aaatacagac   7260
gtgataaatt attagcaact atggaaagat tagatccaac ttatggtgaa atgaaagcta   7320
agttaaatga ctcgtcatta tctccagaag aacactcgaa aataagcgcc aaattgtttg   7380
```

-continued

```
cacgtgaaaa ggctttatta ccaatttatg ctcaaatttc cgttcaattt gctgacttgc   7440

acgatagatc aggtcgtatg ttggccaagg gagttattag aaaggaaatc aaatggactg   7500

atgctagacg tttcttcttc tggagattga gaagaagatt gaacgaggaa tatgttttga   7560

gattgattag tgaacaaatt aaagattcta gcaaattgga aagagttgcc agattgaaga   7620

gttggatgcc aactgttgaa tacgatgatg accaagctgt cagtaactgg attgaagaga   7680

accatgccaa attgcaaaag agagttaatg aattgaaaca agaagtttca agaaccaaga   7740

ttatgagatt attaaaagag gatccaaata gtgcaatttc tgcaatgaaa gactatgttg   7800

aaagattgtc aaaagaagat aaagagaaat tcctcaaggc attgaagtag aagtggtttc   7860

cattaattca actttttaat gacattgaaa gtagtagtag ttgttgtttt ttagatttaa   7920

gtatattata ttatgtaata aattatagaa agtaattata gttttgacgg ttaattgacg   7980

agagtgggaa attggctttt ttgttgctcg tgtgatgaaa cagtgattga cacaaaaaaa   8040

tagacaatga aaac                                                     8054
```

```
<210> SEQ ID NO 3
<211> LENGTH: 2270
<212> TYPE: PRT
<213> ORGANISM: Candida albicans

<400> SEQUENCE: 3

 Met Arg Cys Lys Leu Ser Leu Ile Lys Asn Thr Asn Ser Leu Val His
 1               5                   10                  15

Arg Ser Arg Phe Leu Ile Thr Lys Pro Gln Leu Tyr Ile Pro His Arg
            20                  25                  30

 His Tyr Ile Pro Phe Lys Asn Ile Phe Lys Ser Leu Leu Met Ser Asp
        35                  40                  45

 Gln Ser Pro Ser Pro Ser Pro Ser Asp Ser Leu Ser Tyr Thr Thr Leu
    50                  55                  60

 His Glu Asn Leu Pro Ser His Phe Leu Gly Gly Asn Ser Val Leu Asn
 65                  70                  75                  80

 Ala Glu Pro Ser Lys Val Arg Asp Phe Val Arg Ala His Gln Gly His
                 85                  90                  95

 Thr Val Ile Ser Lys Ile Leu Ile Ala Asn Asn Gly Ile Ala Ala Val
            100                 105                 110

 Lys Glu Ile Arg Ser Val Arg Lys Trp Ala Tyr Glu Thr Phe Gly Asp
        115                 120                 125

 Glu Lys Ala Ile Gln Phe Thr Val Met Ala Thr Pro Glu Asp Leu Glu
    130                 135                 140

 Ala Asn Ala Glu Tyr Ile Arg Met Ala Asp Gln Phe Ile Glu Val Pro
 145                 150                 155                 160

 Gly Gly Thr Asn Asn Asn Asn Tyr Ala Asn Val Asp Leu Ile Val Glu
                 165                 170                 175

 Ile Ala Glu Ser Thr Asn Ala His Ala Val Trp Ala Gly Trp Gly His
            180                 185                 190

 Ala Ser Glu Asn Pro Leu Leu Pro Glu Lys Leu Ala Ala Ser Pro Lys
        195                 200                 205

 Lys Ile Ile Phe Ile Gly Pro Pro Gly Ser Ala Met Arg Ser Leu Gly
    210                 215                 220

 Asp Lys Ile Ser Ser Thr Ile Val Ala Gln His Ala Gln Val Pro Cys
 225                 230                 235                 240

 Ile Pro Trp Ser Gly Thr Gly Val Asp Glu Val Lys Ile Asp Pro Gln
```

-continued

```
                245                 250                 255

Thr Asn Leu Val Ser Val Ala Asp Asp Ile Tyr Ala Lys Gly Cys Cys
            260                 265                 270

Thr Ser Pro Glu Asp Gly Leu Glu Lys Ala Lys Lys Ile Gly Phe Pro
        275                 280                 285

Val Met Ile Lys Ala Ser Glu Gly Gly Gly Gly Lys Gly Ile Arg Lys
    290                 295                 300

Val Asp Asp Glu Lys Asn Phe Ile Thr Leu Tyr Asn Gln Ala Ala Asn
305                 310                 315                 320

Glu Ile Pro Gly Ser Pro Ile Phe Ile Met Lys Leu Ala Gly Asp Ala
                325                 330                 335

Arg His Leu Glu Val Gln Leu Leu Ala Asp Gln Tyr Gly Thr Asn Ile
            340                 345                 350

Ser Leu Phe Gly Arg Asp Cys Ser Val Gln Arg Arg His Gln Lys Ile
        355                 360                 365

Ile Glu Glu Ala Pro Val Thr Ile Ala Arg Lys Glu Thr Phe His Glu
    370                 375                 380

Met Glu Asn Ala Ala Val Arg Leu Gly Lys Leu Val Gly Tyr Val Ser
385                 390                 395                 400

Ala Gly Thr Val Glu Tyr Leu Tyr Ser His Ala Glu Asp Lys Phe Tyr
                405                 410                 415

Phe Leu Glu Leu Asn Pro Arg Leu Gln Val Glu His Pro Thr Thr Glu
            420                 425                 430

Met Val Thr Gly Val Asn Leu Pro Ala Ala Gln Leu Gln Ile Ala Met
        435                 440                 445

Gly Ile Pro Met His Arg Ile Arg Asp Ile Arg Thr Leu Tyr Gly Ala
    450                 455                 460

Asp Pro His Thr Thr Thr Asp Ile Asp Phe Glu Phe Lys Ser Glu Thr
465                 470                 475                 480

Ser Leu Val Ser Gln Arg Arg Pro Thr Pro Lys Gly His Cys Thr Ala
                485                 490                 495

Cys Arg Ile Thr Ser Glu Asp Pro Gly Glu Gly Phe Lys Pro Ser Gly
            500                 505                 510

Gly Ser Leu His Glu Leu Asn Phe Arg Ser Ser Ser Asn Val Trp Gly
        515                 520                 525

Tyr Phe Ser Val Gly Asn Gln Ser Ser Ile His Ser Phe Ser Asp Ser
    530                 535                 540

Gln Phe Gly His Ile Phe Ala Phe Gly Glu Asn Arg Gln Ala Ser Arg
545                 550                 555                 560

Lys His Met Val Val Ala Leu Lys Glu Leu Ser Ile Arg Gly Asp Phe
                565                 570                 575

Arg Thr Thr Val Glu Tyr Leu Ile Lys Leu Leu Glu Thr Pro Asp Phe
            580                 585                 590

Glu Asp Asn Thr Ile Thr Thr Gly Trp Leu Asp Glu Leu Ile Thr Lys
        595                 600                 605

Lys Leu Thr Ala Glu Arg Pro Asp Pro Ile Val Ala Val Val Cys Gly
    610                 615                 620

Ala Val Thr Lys Ala His Ile Gln Ala Glu Glu Glu Lys Lys Glu Tyr
625                 630                 635                 640

Ile Gln Ser Leu Glu Lys Gly Gln Val Pro His Arg Asn Leu Leu Lys
                645                 650                 655

Thr Ile Phe Pro Val Glu Phe Ile Tyr Glu Gly Glu Arg Tyr Lys Phe
            660                 665                 670
```

-continued

```
Thr Ala Thr Lys Ser Ser Glu Asp Lys Tyr Thr Leu Phe Leu Asn Gly
        675                 680                 685

Ser Arg Cys Val Val Gly Ala Arg Ser Leu Ser Asp Gly Gly Leu Leu
    690                 695                 700

Cys Ala Leu Asp Gly Lys Ser His Ser Val Tyr Trp Lys Glu Glu Ala
705                 710                 715                 720

Ser Ala Thr Arg Leu Ser Val Asp Gly Lys Thr Cys Leu Leu Glu Val
                725                 730                 735

Glu Asn Asp Pro Thr Gln Leu Arg Thr Pro Ser Pro Gly Lys Leu Val
            740                 745                 750

Lys Tyr Leu Val Asp Ser Gly Glu His Val Asp Ala Gly Gln Pro Tyr
        755                 760                 765

Ala Glu Val Glu Val Met Lys Met Cys Met Pro Leu Ile Ala Gln Glu
    770                 775                 780

Asn Gly Val Val Gln Leu Ile Lys Gln Pro Gly Ser Thr Val Asn Ala
785                 790                 795                 800

Gly Asp Ile Leu Ala Ile Leu Ala Leu Asp Asp Pro Ser Lys Val Lys
                805                 810                 815

His Ala Lys Pro Phe Glu Gly Thr Leu Pro Ser Met Gly Glu Pro Asn
            820                 825                 830

Val Thr Gly Thr Lys Pro Ala His Lys Phe Asn His Cys Ala Gly Ile
        835                 840                 845

Leu Lys Asn Ile Leu Ala Gly Tyr Asp Asn Gln Val Ile Leu Asn Ser
    850                 855                 860

Thr Leu Lys Ser Leu Gly Glu Val Leu Lys Asp Asn Glu Leu Pro Tyr
865                 870                 875                 880

Ser Glu Trp Gln Gln Gln Ile Ser Ala Leu His Ser Arg Leu Pro Pro
                885                 890                 895

Lys Leu Asp Asp Gly Leu Thr Ala Leu Val Glu Arg Thr Gln Ser Arg
            900                 905                 910

Gly Ala Glu Phe Pro Ala Arg Gln Ile Leu Lys Leu Ile Thr Lys Ser
        915                 920                 925

Ile Ala Glu Asn Gly Asn Asp Met Leu Glu Asp Val Val Ala Pro Leu
    930                 935                 940

Val Ser Ile Ala Thr Ser Tyr Gln Asn Gly Leu Val Glu His Glu Tyr
945                 950                 955                 960

Asp Tyr Phe Ala Ser Leu Ile Asn Glu Tyr Tyr Asp Val Glu Ser Leu
                965                 970                 975

Phe Ser Gly Glu Asn Val Arg Glu Asp Asn Val Ile Leu Lys Leu Arg
            980                 985                 990

Asp Glu Asn Lys Ser Asp Leu Lys Lys Val Ile Gly Ile Gly Leu Ser
        995                 1000                1005

His Ser Arg Val Ser Ala Lys Asn Asn Leu Ile Leu Ala Ile Leu Asp
    1010                1015                1020

Ile Tyr Glu Pro Leu Leu Gln Ser Asn Ser Ser Val Ala Ala Ser Ile
1025                1030                1035                1040

Arg Glu Ala Leu Lys Asn Leu Phe Ile Arg Pro Arg Ala Cys Ala Lys
                1045                1050                1055

Val Ala Leu Lys Ala Arg Glu Ile Leu Ile Gln Cys Ser Leu Pro Ser
            1060                1065                1070

Ile Lys Glu Arg Ser Asp Gln Leu Glu His Ile Leu Arg Ser Ser Val
        1075                1080                1085
```

-continued

```
Val Gln Thr Ser Tyr Gly Glu Ile Phe Ala Lys His Arg Glu Pro Asn
    1090                1095                1100

Leu Glu Ile Ile Arg Glu Val Val Asp Ser Lys His Ile Val Phe Asp
1105                1110                1115                1120

Val Leu Ala Gln Phe Leu Ile Asn Pro Asp Pro Trp Val Ala Ile Ala
                1125                1130                1135

Ala Ala Glu Val Tyr Val Arg Arg Ser Tyr Arg Ala Tyr Asp Leu Gly
            1140                1145                1150

Lys Ile Glu Tyr His Val Asn Asp Arg Leu Pro Ile Val Glu Trp Lys
        1155                1160                1165

Phe Lys Leu Ala Asn Met Gly Ala Ala Gly Val Asn Asp Ala Gln Gln
    1170                1175                1180

Ala Ala Ala Ala Gly Gly Asp Asp Ser Thr Ser Met Lys His Ala Ala
1185                1190                1195                1200

Ser Val Ser Asp Leu Thr Phe Val Val Asp Ser Lys Thr Glu His Ser
                1205                1210                1215

Thr Arg Thr Gly Val Leu Ala Pro Ala Arg His Leu Asp Asp Val Asp
            1220                1225                1230

Glu Thr Leu Thr Ala Ala Leu Glu Gln Phe Gln Pro Ala Asp Ala Ile
        1235                1240                1245

Ser Phe Lys Ala Lys Gly Glu Thr Pro Glu Leu Leu Asn Val Leu Asn
    1250                1255                1260

Ile Val Ile Thr Ser Ile Asp Gly Tyr Ser Asp Glu Asn Glu Tyr Leu
1265                1270                1275                1280

Ser Arg Ile Asn Glu Ile Leu Cys Glu Tyr Lys Glu Glu Leu Ile Ser
                1285                1290                1295

Ala Gly Val Arg Arg Val Thr Phe Val Phe Ala His Gln Ile Gly Gln
            1300                1305                1310

Tyr Pro Lys Tyr Tyr Thr Phe Thr Gly Pro Asp Tyr Glu Glu Asn Lys
        1315                1320                1325

Val Ile Arg His Ile Glu Pro Ala Leu Ala Phe Gln Leu Glu Leu Gly
    1330                1335                1340

Arg Leu Ala Asn Phe Asp Ile Lys Pro Ile Phe Thr Asn Asn Arg Asn
1345                1350                1355                1360

Ile His Val Tyr Asp Ala Ile Gly Lys Asn Ala Pro Ser Asp Lys Arg
                1365                1370                1375

Phe Phe Thr Arg Gly Ile Ile Arg Thr Gly Val Leu Lys Glu Asp Ile
            1380                1385                1390

Ser Ile Ser Glu Tyr Leu Ile Ala Glu Ser Asn Arg Leu Met Asn Asp
        1395                1400                1405

Ile Leu Asp Thr Leu Glu Val Ile Asp Thr Ser Asn Ser Asp Leu Asn
    1410                1415                1420

His Ile Phe Ile Asn Phe Ser Asn Ala Phe Asn Val Gln Ala Ser Asp
1425                1430                1435                1440

Val Glu Ala Ala Phe Gly Ser Phe Leu Glu Arg Phe Gly Arg Arg Leu
                1445                1450                1455

Trp Arg Leu Arg Val Thr Gly Ala Glu Ile Arg Ile Val Cys Thr Asp
            1460                1465                1470

Pro Gln Gly Thr Ser Phe Pro Leu Arg Ala Ile Ile Asn Asn Val Ser
        1475                1480                1485

Gly Tyr Val Val Lys Ser Glu Leu Tyr Leu Glu Val Lys Asn Pro Lys
    1490                1495                1500

Gly Glu Trp Val Phe Lys Ser Ile Gly His Pro Gly Ser Met His Leu
```

-continued

```
1505                1510                1515                1520

Arg Pro Ile Ser Thr Pro Tyr Pro Val Lys Glu Ser Leu Gln Pro Lys
                1525                1530                1535

Arg Tyr Lys Ala His Asn Met Gly Thr Thr Tyr Val Tyr Asp Phe Pro
            1540                1545                1550

Glu Leu Phe Arg Gln Ala Thr Ile Ser Gln Trp Lys Lys Tyr Gly Lys
        1555                1560                1565

Lys Val Pro Lys Asp Val Phe Val Ser Leu Glu Leu Ile Thr Asp Glu
    1570                1575                1580

Thr Asp Ser Leu Ile Ala Val Glu Arg Asp Pro Gly Ala Asn Lys Ile
1585                1590                1595                1600

Gly Met Val Gly Phe Lys Val Thr Ala Lys Thr Pro Glu Tyr Pro His
                1605                1610                1615

Gly Arg Gln Leu Ile Ile Val Ala Asn Asp Ile Thr His Lys Ile Gly
            1620                1625                1630

Ser Phe Gly Pro Glu Glu Asp Asn Tyr Phe Asn Lys Cys Thr Glu Leu
        1635                1640                1645

Ala Arg Lys Leu Gly Ile Pro Arg Ile Tyr Leu Ser Ala Asn Ser Gly
    1650                1655                1660

Ala Arg Ile Gly Val Ala Glu Glu Leu Ile Pro Leu Tyr Gln Val Ala
1665                1670                1675                1680

Trp Asn Glu Glu Gly Ser Pro Asp Lys Gly Phe Arg Tyr Leu Tyr Leu
                1685                1690                1695

Ser Thr Ala Ala Lys Glu Ser Leu Glu Lys Asp Gly Lys Ser Asp Ser
            1700                1705                1710

Val Val Thr Glu Arg Ile Val Glu Lys Gly Glu Glu Arg His Val Ile
        1715                1720                1725

Lys Ala Ile Ile Gly Ala Glu Asp Gly Leu Gly Val Glu Cys Leu Lys
    1730                1735                1740

Gly Ser Gly Leu Ile Ala Gly Ala Thr Ser Arg Ala Tyr Lys Asp Ile
1745                1750                1755                1760

Phe Thr Ile Thr Leu Val Thr Cys Arg Ser Val Gly Ile Gly Ala Tyr
                1765                1770                1775

Leu Val Arg Leu Gly Gln Arg Ala Ile Gln Ile Asp Gly Gln Pro Ile
            1780                1785                1790

Ile Leu Thr Gly Ala Pro Ala Ile Asn Lys Leu Leu Gly Arg Glu Val
        1795                1800                1805

Tyr Ser Ser Asn Leu Gln Leu Gly Gly Thr Gln Ile Met Tyr Asn Asn
    1810                1815                1820

Gly Val Ser His Leu Thr Ala Asn Asp Asp Leu Ala Gly Val Glu Lys
1825                1830                1835                1840

Ile Met Glu Trp Leu Ser Tyr Val Pro Ala Lys Arg Gly Leu Pro Val
                1845                1850                1855

Pro Ile Leu Glu Ser Glu Asp Ser Trp Asp Arg Asp Val Asp Tyr Tyr
            1860                1865                1870

Pro Pro Lys Gln Glu Ala Phe Asp Val Arg Trp Met Ile Gln Gly Arg
        1875                1880                1885

Glu Val Asp Gly Glu Tyr Glu Ser Gly Leu Phe Asp Lys Asp Ser Phe
    1890                1895                1900

Gln Glu Thr Leu Ser Gly Trp Ala Lys Gly Val Val Val Gly Arg Ala
1905                1910                1915                1920

Arg Leu Gly Gly Ile Pro Ile Gly Val Ile Gly Val Glu Thr Arg Thr
                1925                1930                1935
```

-continued

```
Val Glu Asn Leu Ile Pro Ala Asp Pro Ala Asn Pro Asp Ser Thr Glu
            1940                1945                1950

Ser Leu Ile Gln Glu Ala Gly Gln Val Trp Tyr Pro Asn Ser Ala Phe
        1955                1960                1965

Lys Thr Ala Gln Ala Ile Asn Asp Phe Asn Asn Gly Glu Gln Leu Pro
    1970                1975                1980

Leu Met Ile Leu Ala Asn Trp Arg Gly Phe Ser Gly Gly Gln Arg Asp
1985                1990                1995                2000

Met Tyr Asn Glu Val Leu Lys Tyr Gly Ser Phe Ile Val Asp Ala Leu
                2005                2010                2015

Val Asp Phe Lys Gln Pro Ile Phe Thr Tyr Ile Pro Pro Asn Gly Glu
            2020                2025                2030

Leu Arg Gly Gly Ser Trp Val Val Val Asp Pro Thr Ile Asn Ser Asp
        2035                2040                2045

Met Met Glu Met Tyr Ala Asp Val Asp Ser Arg Ala Gly Val Leu Glu
    2050                2055                2060

Pro Glu Gly Met Val Gly Ile Lys Tyr Arg Arg Asp Lys Leu Leu Ala
2065                2070                2075                2080

Thr Met Glu Arg Leu Asp Pro Thr Tyr Gly Glu Met Lys Ala Lys Leu
                2085                2090                2095

Asn Asp Ser Ser Leu Ser Pro Glu Glu His Ser Lys Ile Ser Ala Lys
            2100                2105                2110

Leu Phe Ala Arg Glu Lys Ala Leu Leu Pro Ile Tyr Ala Gln Ile Ser
        2115                2120                2125

Val Gln Phe Ala Asp Leu His Asp Arg Ser Gly Arg Met Leu Ala Lys
    2130                2135                2140

Gly Val Ile Arg Lys Glu Ile Lys Trp Thr Asp Ala Arg Arg Phe Phe
2145                2150                2155                2160

Phe Trp Arg Leu Arg Arg Arg Leu Asn Glu Glu Tyr Val Leu Arg Leu
                2165                2170                2175

Ile Ser Glu Gln Ile Lys Asp Ser Ser Lys Leu Glu Arg Val Ala Arg
            2180                2185                2190

Leu Lys Ser Trp Met Pro Thr Val Glu Tyr Asp Asp Asp Gln Ala Val
        2195                2200                2205

Ser Asn Trp Ile Glu Glu Asn His Ala Lys Leu Gln Lys Arg Val Asn
    2210                2215                2220

Glu Leu Lys Gln Glu Val Ser Arg Thr Lys Ile Met Arg Leu Leu Lys
2225                2230                2235                2240

Glu Asp Pro Asn Ser Ala Ile Ser Ala Met Lys Asp Tyr Val Glu Arg
                2245                2250                2255

Leu Ser Lys Glu Asp Lys Glu Lys Phe Leu Lys Ala Leu Lys
            2260                2265                2270
```